(12) United States Patent
Mathis

(10) Patent No.: US 7,549,984 B2
(45) Date of Patent: Jun. 23, 2009

(54) METHOD OF COMPRESSING A PORTION OF A LUNG

(75) Inventor: Mark L. Mathis, Fremont, CA (US)

(73) Assignee: PneumRx, Inc., Mountain View, CA (US)

( * ) Notice: Subject to any disclaimer, the term of this patent is extended or adjusted under 35 U.S.C. 154(b) by 0 days.

(21) Appl. No.: 11/153,253

(22) Filed: Jun. 14, 2005

(65) Prior Publication Data

US 2006/0009748 A1    Jan. 12, 2006

Related U.S. Application Data

(60) Provisional application No. 60/580,565, filed on Jun. 16, 2004.

(51) Int. Cl.
*A61M 31/00* (2006.01)
(52) U.S. Cl. ...................................... 604/509
(58) Field of Classification Search ............ 128/207.14, 128/207.15, 200.26, 203.12, 898; 606/108, 606/194; 604/96.01, 93.01, 509, 500, 122, 604/129, 99.03
See application file for complete search history.

(56) References Cited

U.S. PATENT DOCUMENTS

| | | | |
|---|---|---|---|
| 3,559,652 A | 2/1971 | Banitt et al. | |
| 3,834,394 A | 9/1974 | Hunter et al. | |
| 4,013,080 A | 3/1977 | Froning | |
| 4,153,058 A | 5/1979 | Nehme | |
| 4,233,984 A * | 11/1980 | Walling ............... | 128/207.14 |
| 4,340,046 A | 7/1982 | Cox | |
| 4,364,392 A | 12/1982 | Strother et al. | |
| 4,402,319 A | 9/1983 | Handa et al. | |
| 4,479,792 A | 10/1984 | Lazarus et al. | |
| 4,532,935 A | 8/1985 | Wang | |
| 4,702,260 A | 10/1987 | Wang | |
| 4,705,517 A | 11/1987 | DiPisa, Jr. | |
| 4,739,760 A | 4/1988 | Chin et al. | |
| 4,766,906 A | 8/1988 | Wang | |
| 4,769,017 A | 9/1988 | Fath et al. | |

(Continued)

FOREIGN PATENT DOCUMENTS

FR        2840796        12/2003

(Continued)

OTHER PUBLICATIONS

Hermanson, Greg T. 1996. *Bioconjugate Techniques*. San Diego: Academic Press, Inc.

(Continued)

*Primary Examiner*—Nicholas D Lucchesi
*Assistant Examiner*—Christopher D Koharski
(74) *Attorney, Agent, or Firm*—Townsend and Townsend and Crew LLP

(57) ABSTRACT

The invention provides methods of performing lung volume reduction to treat a patient. One aspect of the invention provides a method of compressing a first portion of a lung of a patient including the following steps: providing a vent connecting the first portion of the lung to the exterior of the patient; isolating the first portion of the lung from a second portion of the lung adjacent the first portion; and delivering pressurized fluid to the second portion of the lung to compress the first portion of the lung.

17 Claims, 23 Drawing Sheets

U.S. PATENT DOCUMENTS

| | | | |
|---|---|---|---|
| 4,819,664 A | 4/1989 | Nazari | |
| 4,828,561 A | 5/1989 | Woodroof | |
| 4,880,015 A | 11/1989 | Nierman | |
| 5,056,529 A | 10/1991 | de Groot | |
| 5,084,012 A | 1/1992 | Kelman | |
| 5,108,368 A | 4/1992 | Hammerslag et al. | |
| 5,165,420 A | 11/1992 | Strickland | |
| 5,186,167 A | 2/1993 | Kolobow | |
| 5,190,546 A | 3/1993 | Jervis | |
| 5,219,895 A | 6/1993 | Kelman | |
| 5,240,011 A | 8/1993 | Assa | |
| 5,261,889 A | 11/1993 | Laine et al. | |
| 5,312,329 A | 5/1994 | Beaty et al. | |
| 5,312,331 A | 5/1994 | Knoepfler | |
| 5,315,992 A * | 5/1994 | Dalton | 128/207.15 |
| 5,334,183 A | 8/1994 | Wuchinich | |
| 5,354,287 A | 10/1994 | Wacks | |
| 5,385,606 A | 1/1995 | Kowanko | |
| 5,423,830 A | 6/1995 | Schneebaum et al. | |
| 5,484,401 A | 1/1996 | Rodriguez et al. | |
| 5,514,536 A | 5/1996 | Taylor | |
| 5,526,821 A | 6/1996 | Jamshidi | |
| 5,549,904 A | 8/1996 | Juergensen et al. | |
| 5,599,294 A | 2/1997 | Edwards et al. | |
| 5,660,175 A * | 8/1997 | Dayal | 128/207.15 |
| 5,660,185 A | 8/1997 | Shmulewitz et al. | |
| 5,697,365 A | 12/1997 | Pell | |
| 5,735,264 A | 4/1998 | Siczek et al. | |
| 5,736,132 A | 4/1998 | Juergensen et al. | |
| 5,750,657 A | 5/1998 | Edwardson et al. | |
| 5,846,235 A | 12/1998 | Pasricha et al. | |
| 5,916,210 A | 6/1999 | Winston | |
| 5,916,212 A | 6/1999 | Baust et al. | |
| 5,938,635 A | 8/1999 | Kuhle | |
| 5,954,636 A * | 9/1999 | Schwartz et al. | 600/120 |
| 5,954,766 A | 9/1999 | Zadno-Azizi et al. | |
| 5,957,919 A | 9/1999 | Laufer | |
| 5,964,770 A | 10/1999 | Flomenblit et al. | |
| 5,972,026 A | 10/1999 | Laufer et al. | |
| 5,978,697 A | 11/1999 | Maytal et al. | |
| 6,066,090 A | 5/2000 | Yoon | |
| 6,080,113 A | 6/2000 | Heneveld et al. | |
| 6,083,255 A | 7/2000 | Laufer et al. | |
| 6,174,323 B1 | 1/2001 | Biggs et al. | |
| 6,183,498 B1 | 2/2001 | DeVore et al. | |
| 6,200,333 B1 | 3/2001 | Laufer | |
| 6,258,100 B1 | 7/2001 | Alferness et al. | |
| 6,267,732 B1 | 7/2001 | Heneveld et al. | |
| 6,273,907 B1 | 8/2001 | Laufer | |
| 6,283,988 B1 | 9/2001 | Laufer et al. | |
| 6,283,989 B1 | 9/2001 | Laufer et al. | |
| 6,287,290 B1 * | 9/2001 | Perkins et al. | 604/516 |
| 6,287,304 B1 | 9/2001 | Eggers et al. | |
| 6,293,951 B1 | 9/2001 | Alferness et al. | |
| 6,299,633 B1 | 10/2001 | Laufer | |
| 6,310,166 B1 | 10/2001 | Hickey et al. | |
| 6,312,428 B1 | 11/2001 | Eggers et al. | |
| 6,315,737 B1 | 11/2001 | Skinner | |
| 6,328,689 B1 | 12/2001 | Gonzalez et al. | |
| 6,328,701 B1 | 12/2001 | Terwilliger | |
| 6,352,503 B1 | 3/2002 | Matsui et al. | |
| 6,372,229 B1 | 4/2002 | Ollerenshaw et al. | |
| 6,379,373 B1 | 4/2002 | Sawhney et al. | |
| 6,387,044 B1 | 5/2002 | Tachibana et al. | |
| 6,390,967 B1 | 5/2002 | Forman et al. | |
| 6,398,775 B1 | 6/2002 | Perkins et al. | |
| 6,402,701 B1 | 6/2002 | Kaplan et al. | |
| 6,402,754 B1 | 6/2002 | Gonzalez | |
| 6,411,852 B1 | 6/2002 | Danek et al. | |
| 6,416,554 B1 | 7/2002 | Alferness et al. | |
| 6,443,944 B1 | 9/2002 | Doshi et al. | |
| 6,447,534 B2 | 9/2002 | Cragg et al. | |
| 6,464,648 B1 | 10/2002 | Nakamura | |
| 6,478,730 B1 | 11/2002 | Bala et al. | |
| 6,485,407 B2 | 11/2002 | Alferness et al. | |
| 6,485,436 B1 | 11/2002 | Truckai et al. | |
| 6,488,673 B1 | 12/2002 | Laufer et al. | |
| 6,491,706 B1 | 12/2002 | Alferness et al. | |
| 6,494,844 B1 | 12/2002 | Van Bladel et al. | |
| 6,494,897 B2 | 12/2002 | Sterman et al. | |
| 6,509,031 B1 | 1/2003 | Miller et al. | |
| 6,514,290 B1 | 2/2003 | Loomas | |
| 6,514,522 B2 | 2/2003 | Domb | |
| 6,527,761 B1 | 3/2003 | Soltesz et al. | |
| 6,537,195 B2 | 3/2003 | Forman | |
| 6,537,314 B2 | 3/2003 | Langberg et al. | |
| 6,540,694 B1 | 4/2003 | Van Bladel et al. | |
| 6,540,716 B1 | 4/2003 | Holm | |
| 6,549,800 B1 | 4/2003 | Atalar et al. | |
| 6,551,255 B2 | 4/2003 | Van Bladel et al. | |
| 6,551,302 B1 | 4/2003 | Rosinko et al. | |
| 6,552,172 B2 | 4/2003 | Marx et al. | |
| 6,558,337 B2 | 5/2003 | Dvorak et al. | |
| 6,568,387 B2 | 5/2003 | Davenport et al. | |
| 6,569,166 B2 | 5/2003 | Gonzalez | |
| 6,577,893 B1 | 6/2003 | Besson et al. | |
| 6,585,639 B1 * | 7/2003 | Kotmel et al. | 600/116 |
| 6,589,161 B2 | 7/2003 | Corcoran | |
| 6,592,559 B1 | 7/2003 | Pakter et al. | |
| 6,592,594 B2 | 7/2003 | Rimbaugh et al. | |
| 6,599,311 B1 | 7/2003 | Biggs et al. | |
| 6,610,043 B1 | 8/2003 | Ingenito | |
| 6,622,731 B2 | 9/2003 | Daniel et al. | |
| 6,629,951 B2 | 10/2003 | Laufer et al. | |
| 6,632,222 B1 | 10/2003 | Edwards et al. | |
| 6,632,239 B2 | 10/2003 | Snyder et al. | |
| 6,632,243 B1 | 10/2003 | Zadno-Azizi et al. | |
| 6,634,363 B1 | 10/2003 | Danek et al. | |
| 6,638,275 B1 | 10/2003 | McGaffigan et al. | |
| 6,652,516 B1 | 11/2003 | Gough | |
| 6,652,520 B2 | 11/2003 | Moorman et al. | |
| 6,653,525 B2 | 11/2003 | Ingenito et al. | |
| 6,663,624 B2 | 12/2003 | Edwards et al. | |
| 6,679,264 B1 | 1/2004 | Deem et al. | |
| 6,682,520 B2 * | 1/2004 | Ingenito | 604/514 |
| 6,685,626 B2 | 2/2004 | Wironen | |
| 6,689,072 B2 | 2/2004 | Kaplan et al. | |
| 6,690,976 B2 | 2/2004 | Fenn et al. | |
| 6,692,494 B1 | 2/2004 | Cooper et al. | |
| 6,694,979 B2 | 2/2004 | Deem et al. | |
| 6,695,791 B2 | 2/2004 | Gonzalez | |
| 6,709,401 B2 | 3/2004 | Perkins et al. | |
| 6,709,408 B2 | 3/2004 | Fisher | |
| 6,709,456 B2 | 3/2004 | Langberg et al. | |
| 6,712,812 B2 | 3/2004 | Roschak et al. | |
| 6,716,180 B2 | 4/2004 | Fontenot | |
| 6,723,095 B2 | 4/2004 | Hammerslag | |
| 6,730,044 B2 | 5/2004 | Stephens et al. | |
| 6,736,822 B2 | 5/2004 | McClellan et al. | |
| 6,749,606 B2 | 6/2004 | Keast et al. | |
| 6,752,767 B2 | 6/2004 | Turovskiy et al. | |
| 6,752,812 B1 | 6/2004 | Truwit | |
| 6,758,824 B1 | 7/2004 | Miller et al. | |
| 6,768,425 B2 | 7/2004 | Flaherty et al. | |
| 6,770,066 B1 | 8/2004 | Weaver et al. | |
| 6,770,070 B1 | 8/2004 | Balbierz | |
| 6,789,545 B2 | 9/2004 | Littrup et al. | |
| 6,790,172 B2 | 9/2004 | Alferness et al. | |
| 6,790,185 B1 | 9/2004 | Fisher et al. | |
| 6,797,001 B2 | 9/2004 | Mathis et al. | |
| 6,807,446 B2 | 10/2004 | Fenn et al. | |
| 6,808,525 B2 | 10/2004 | Latterell et al. | |
| 6,817,973 B2 | 11/2004 | Merril et al. | |
| 6,825,091 B2 | 11/2004 | Bae et al. | |

| | | | | | | |
|---|---|---|---|---|---|---|
| 6,827,086 B2 | 12/2004 | Shuman | | 2004/0024356 A1 | 2/2004 | Tanaka |
| 6,830,756 B2 | 12/2004 | Hnojewyj | | 2004/0030262 A1 | 2/2004 | Fisher et al. |
| 6,840,243 B2 | 1/2005 | Deem et al. | | 2004/0031494 A1 | 2/2004 | Danek et al. |
| 6,840,948 B2 | 1/2005 | Albrecht et al. | | 2004/0038868 A1 | 2/2004 | Ingenito |
| 6,840,952 B2 | 1/2005 | Saker et al. | | 2004/0040555 A1 | 3/2004 | Tanaka |
| 6,843,767 B2 | 1/2005 | Corcoran et al. | | 2004/0049187 A1 | 3/2004 | Burnett et al. |
| 6,849,262 B2 | 2/2005 | Ollerenshaw et al. | | 2004/0052850 A1 | 3/2004 | Schankereli |
| 6,852,108 B2 | 2/2005 | Barry et al. | | 2004/0055606 A1 | 3/2004 | Hendricksen et al. |
| 6,860,847 B2 | 3/2005 | Alferness et al. | | 2004/0059263 A1 | 3/2004 | DeVore et al. |
| 6,863,676 B2 | 3/2005 | Lee et al. | | 2004/0063613 A1 | 4/2004 | Rolke et al. |
| 6,875,209 B2 | 4/2005 | Zvuloni et al. | | 2004/0072756 A1 | 4/2004 | Wilkie et al. |
| 6,878,106 B1 | 4/2005 | Herrmann | | 2004/0073155 A1 | 4/2004 | Laufer et al. |
| 6,878,141 B1 * | 4/2005 | Perkins et al. ............... 604/516 | | 2004/0073191 A1 | 4/2004 | Soltesz et al. |
| 6,886,558 B2 | 5/2005 | Tanaka | | 2004/0073201 A1 | 4/2004 | Cooper et al. |
| 6,901,927 B2 | 6/2005 | Deem et al. | | 2004/0073241 A1 | 4/2004 | Barry et al. |
| 6,902,526 B2 | 6/2005 | Katzman | | 2004/0078054 A1 | 4/2004 | Biggs et al. |
| 6,902,536 B2 | 6/2005 | Manna et al. | | 2004/0081676 A1 | 4/2004 | Schankereli et al. |
| 6,904,909 B2 | 6/2005 | Andreas et al. | | 2004/0120849 A1 | 6/2004 | Stewart et al. |
| 6,908,440 B2 | 6/2005 | Fisher | | 2004/0133168 A1 | 7/2004 | Salcudean et al. |
| 6,918,881 B2 | 7/2005 | Miller et al. | | 2004/0158228 A1 | 8/2004 | Perkins |
| 6,936,014 B2 | 8/2005 | Vetter et al. | | 2004/0172058 A1 | 9/2004 | Edwards et al. |
| 6,942,627 B2 | 9/2005 | Huitema | | 2004/0176801 A1 | 9/2004 | Edwards et al. |
| 6,945,942 B2 | 9/2005 | Van Bladel et al. | | 2004/0210248 A1 | 10/2004 | Gordon et al. |
| 6,962,587 B2 | 11/2005 | Johnson et al. | | 2004/0211434 A1 | 10/2004 | Loomas et al. |
| 6,964,662 B2 | 11/2005 | Kidooka | | 2004/0220556 A1 | 11/2004 | Cooper et al. |
| 6,967,673 B2 | 11/2005 | Ozawa et al. | | 2004/0225254 A1 | 11/2004 | Tanaka et al. |
| 2002/0007831 A1 * | 1/2002 | Davenport et al. ..... 128/200.24 | | 2004/0231674 A1 | 11/2004 | Tanaka |
| 2002/0026188 A1 | 2/2002 | Balbierz et al. | | 2004/0234575 A1 | 11/2004 | Horres et al. |
| 2002/0042564 A1 | 4/2002 | Cooper et al. | | 2004/0237966 A1 | 12/2004 | Tanaka |
| 2002/0042565 A1 | 4/2002 | Cooper et al. | | 2004/0244802 A1 | 12/2004 | Tanaka |
| 2002/0062120 A1 | 5/2002 | Perkins et al. | | 2004/0244803 A1 | 12/2004 | Tanaka |
| 2002/0077593 A1 | 6/2002 | Perkins et al. | | 2005/0004599 A1 | 1/2005 | McNally-Heintzelman et al. |
| 2002/0091379 A1 | 7/2002 | Danek et al. | | 2005/0013788 A1 | 1/2005 | Held et al. |
| 2002/0111620 A1 | 8/2002 | Cooper et al. | | 2005/0015106 A1 | 1/2005 | Perkins et al. |
| 2002/0112729 A1 | 8/2002 | DeVore et al. | | 2005/0043751 A1 | 2/2005 | Phan et al. |
| 2002/0128647 A1 | 9/2002 | Roschak et al. | | 2005/0043752 A1 | 2/2005 | Phan et al. |
| 2002/0138074 A1 | 9/2002 | Keast et al. | | 2005/0049615 A1 | 3/2005 | Cooper et al. |
| 2002/0161399 A1 | 10/2002 | Cruise et al. | | 2005/0060041 A1 | 3/2005 | Phan et al. |
| 2002/0176893 A1 | 11/2002 | Wironen et al. | | 2005/0060042 A1 | 3/2005 | Phan et al. |
| 2002/0183244 A1 | 12/2002 | Ollerenshaw et al. | | 2005/0061322 A1 | 3/2005 | Freitag |
| 2002/0183838 A1 | 12/2002 | Liddicoat et al. | | 2005/0085801 A1 | 4/2005 | Cooper et al. |
| 2002/0185135 A1 * | 12/2002 | Amar .................... 128/207.15 | | 2005/0096529 A1 | 5/2005 | Cooper et al. |
| 2002/0188171 A1 | 12/2002 | Alferness et al. | | 2005/0107783 A1 | 5/2005 | Tom et al. |
| 2003/0018318 A1 | 1/2003 | Melsky | | 2005/0119614 A1 | 6/2005 | Mesky |
| 2003/0029452 A1 | 2/2003 | Suki et al. | | 2005/0281739 A1 | 12/2005 | Gong et al. |
| 2003/0050648 A1 | 3/2003 | Alferness et al. | | 2005/0281740 A1 | 12/2005 | Gong et al. |
| 2003/0051733 A1 | 3/2003 | Kotmel et al. | | 2005/0281796 A1 | 12/2005 | Gong et al. |
| 2003/0055331 A1 | 3/2003 | Kotmel et al. | | 2005/0281797 A1 | 12/2005 | Gong et al. |
| 2003/0069488 A1 | 4/2003 | Alferness et al. | | 2005/0281798 A1 | 12/2005 | Gong et al. |
| 2003/0070676 A1 | 4/2003 | Cooper et al. | | 2005/0281799 A1 | 12/2005 | Gong et al. |
| 2003/0070682 A1 | 4/2003 | Wilson et al. | | 2005/0281800 A1 | 12/2005 | Gong et al. |
| 2003/0070683 A1 | 4/2003 | Deem et al. | | 2005/0281801 A1 | 12/2005 | Gong et al. |
| 2003/0075170 A1 | 4/2003 | Deem et al. | | 2005/0281802 A1 | 12/2005 | Gong et al. |
| 2003/0083671 A1 | 5/2003 | Rimbaugh et al. | | 2005/0282748 A1 | 12/2005 | Gong et al. |
| 2003/0100921 A1 | 5/2003 | Addis et al. | | 2005/0288549 A1 | 12/2005 | Mathis |
| 2003/0109866 A1 | 6/2003 | Edwards et al. | | 2005/0288550 A1 | 12/2005 | Mathis |
| 2003/0127090 A1 | 7/2003 | Gifford et al. | | 2005/0288684 A1 | 12/2005 | Aronson et al. |
| 2003/0130657 A1 | 7/2003 | Tom et al. | | 2005/0288702 A1 | 12/2005 | McGurk et al. |
| 2003/0154988 A1 | 8/2003 | DeVore et al. | | 2006/0004400 A1 | 1/2006 | McGurk et al. |
| 2003/0158515 A1 | 8/2003 | Gonzalez et al. | | 2006/0009801 A1 | 1/2006 | McGurk et al. |
| 2003/0159700 A1 | 8/2003 | Laufer et al. | | 2006/0025815 A1 | 2/2006 | McGurk et al. |
| 2003/0181356 A1 | 9/2003 | Ingenito | | 2006/0167416 A1 | 7/2006 | Mathis et al. |
| 2003/0181922 A1 | 9/2003 | Alferness | | 2007/0221230 A1 | 9/2007 | Thompson et al. |
| 2003/0183235 A1 | 10/2003 | Rimbaugh et al. | | | | |
| 2003/0191496 A1 | 10/2003 | Edwards et al. | | FOREIGN PATENT DOCUMENTS | | |
| 2003/0195385 A1 | 10/2003 | DeVore | | | | |
| 2003/0195511 A1 | 10/2003 | Barry | | GB | 2324729 B | 1/2002 |
| 2003/0212337 A1 | 11/2003 | Sirokman | | WO | WO 00/13592 A1 | 3/2000 |
| 2003/0212412 A1 | 11/2003 | Dillard et al. | | WO | WO 01/13839 A1 | 3/2001 |
| 2003/0228344 A1 | 12/2003 | Fields | | WO | WO 02/00270 A1 | 1/2002 |
| 2003/0233099 A1 | 12/2003 | Danaek et al. | | WO | WO 02/00275 A1 | 1/2002 |
| 2004/0010209 A1 | 1/2004 | Sirokman | | WO | WO 02/02158 A1 | 1/2002 |
| 2004/0010289 A1 | 1/2004 | Biggs et al. | | WO | WO 03/077768 A1 | 9/2003 |

| | | |
|---|---|---|
| WO | WO 2004/062505 A1 | 7/2004 |
| WO | WO 2004/086977 A1 | 10/2004 |
| WO | WO 2006/009682 A2 | 1/2006 |
| WO | WO 2008/036763 A2 | 3/2008 |

OTHER PUBLICATIONS

Lam, K.N. Sin Fai el al. 1998. X-Ray Diagnosis: A Physician's Approach. Singapore: Springer.

Rowe, Raymond C., et al. 2003. *Handbook of Pharmaceutical Excipients* 4th Edition. London: Pharmaceutical Press.

Slone, Richard M. et al. 2000. Body CT: A Practical Approach. New York: McGraw-Hill.

Stout, George H. et al. 1989. X-Ray Structure Determination: A Practical Guide, 2nd Edition. New York: John Wiley & Sons.

The United States Pharmacopeia, 29th Revision. 2008. The United States Pharmacopeial Convention.

Mathis, M., U.S. Appl. No. 11/286,445 entitiled "Steerable Device for Accessing a Target Site and Methods", filed Nov. 23, 2005.

International Search Report and Written Opinion of PCT Application No. PCT/US05/20943, dated Jul. 14, 2008, 6 pages total.

* cited by examiner

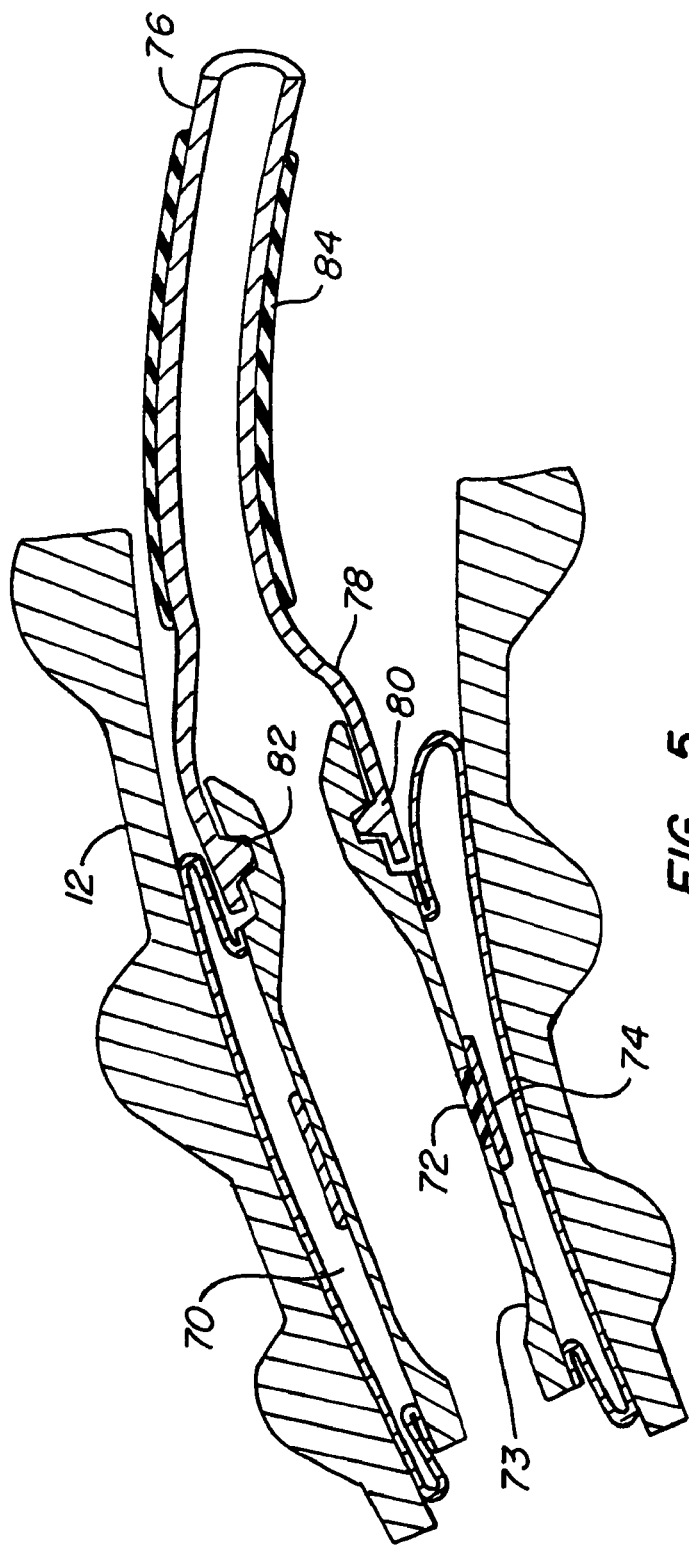
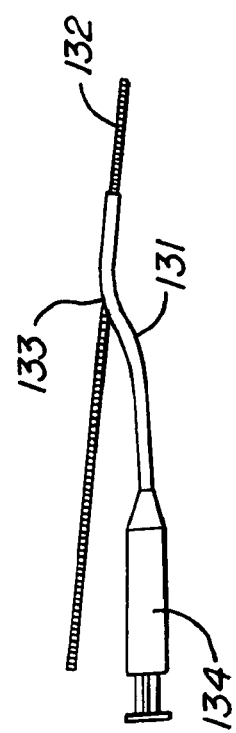
FIG. 5
FIG. 8

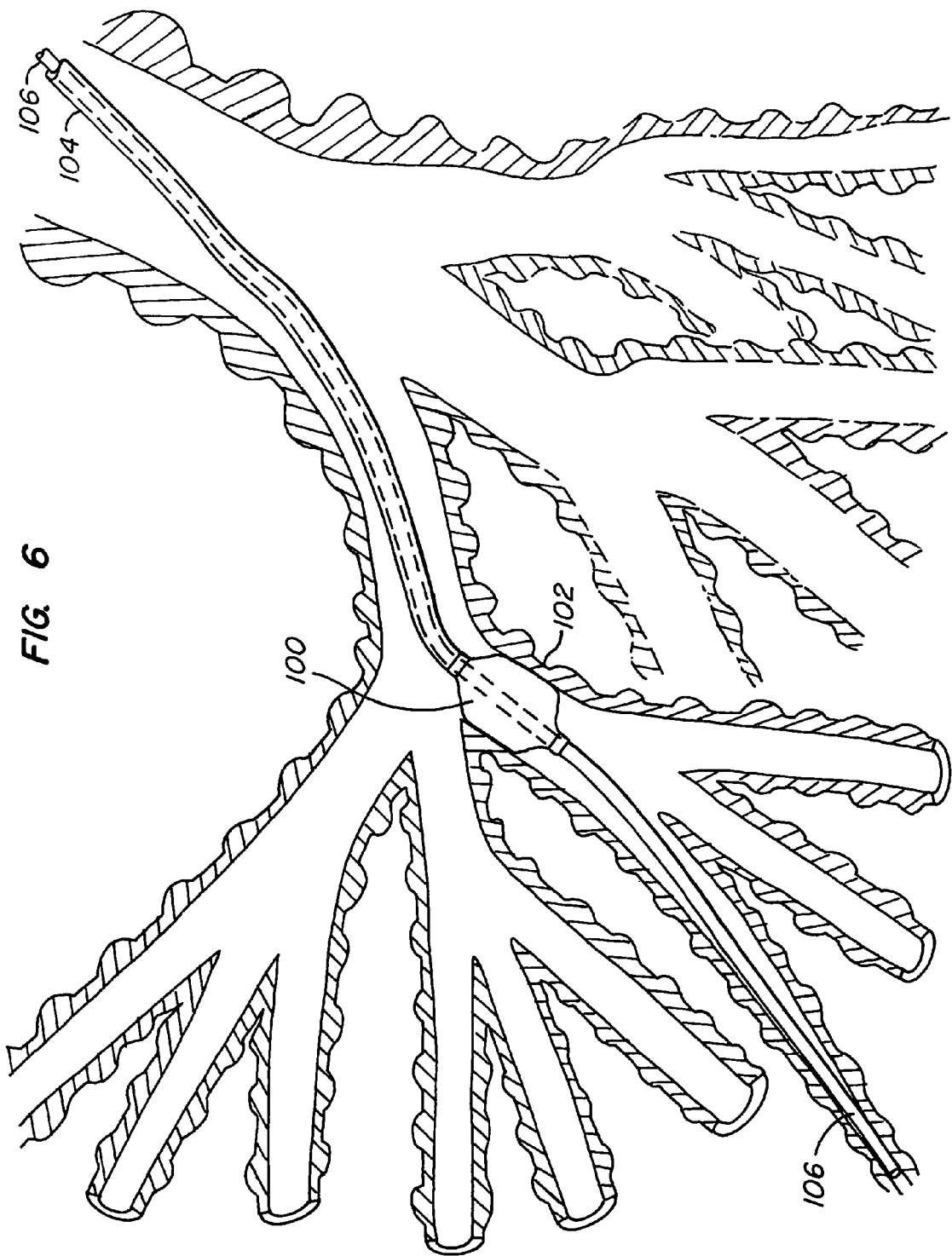

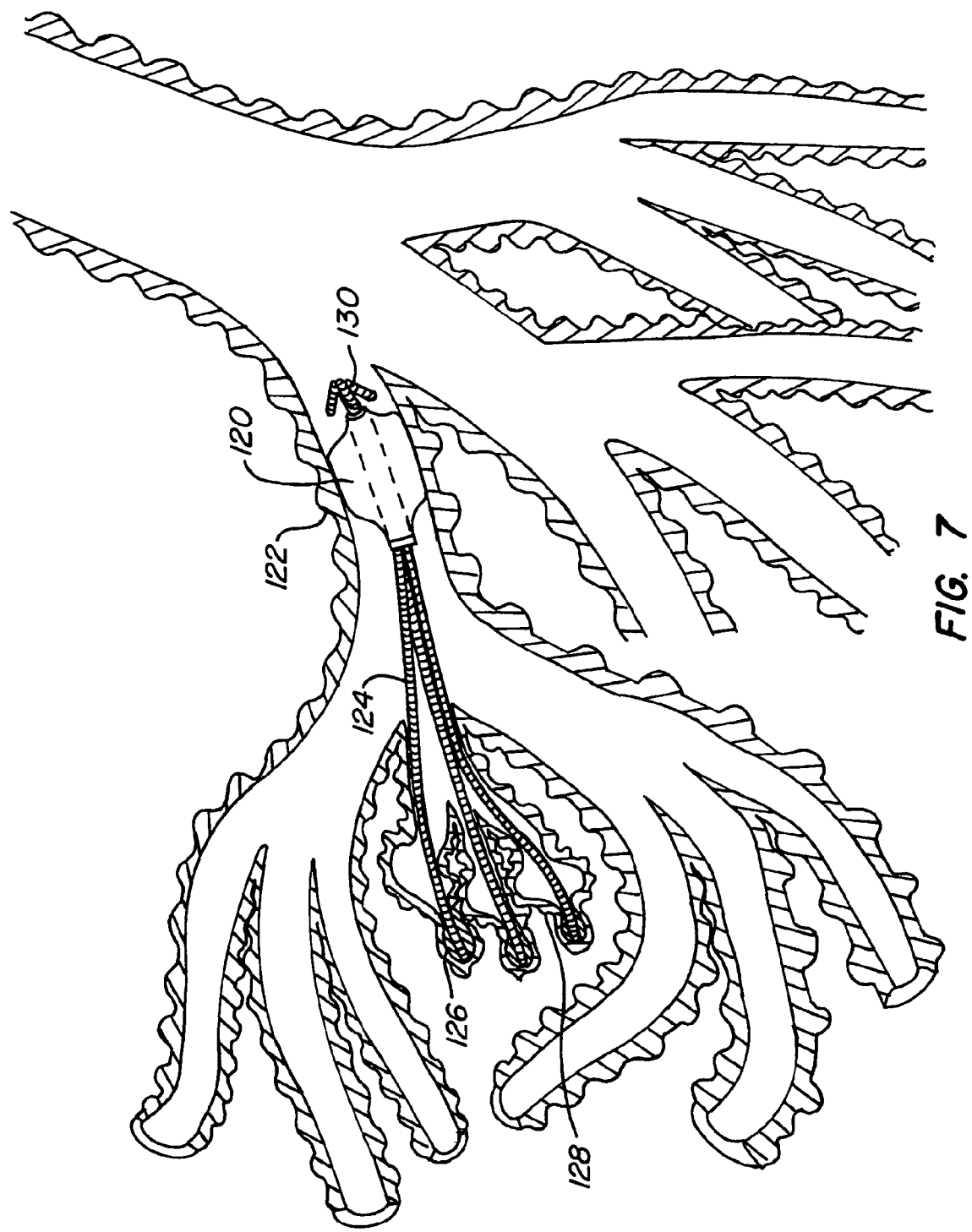

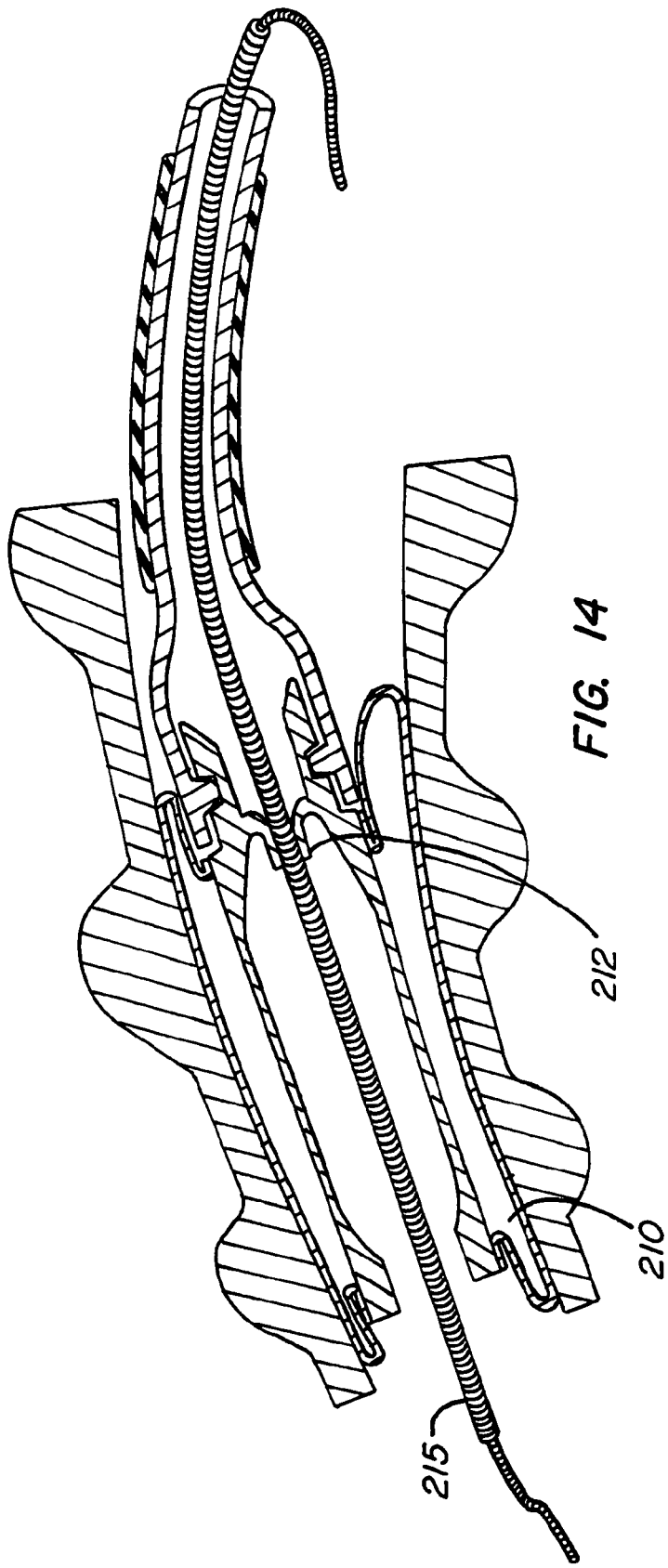
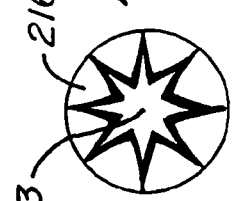
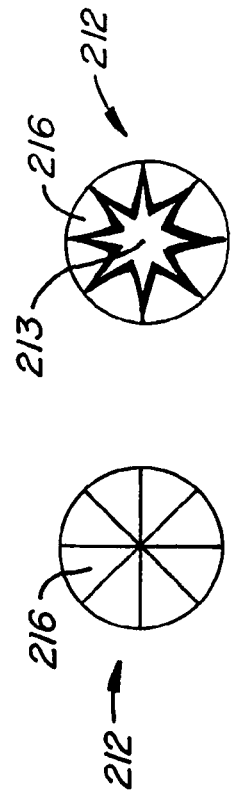

METHOD OF COMPRESSING A PORTION OF A LUNG

CROSS-REFERENCE

This application claims the benefit of U.S. Provisional Application No. 60/580,565, filed Jun. 16, 2004, which is incorporated herein by reference in its entirety.

BACKGROUND OF THE INVENTION

The primary role of the lung is to perform the function of breathing which assists in the intake of oxygen and removal of carbon dioxide from the body. The oxygen in air is inhaled through the mouth and trachea to the main bronchi. The bronchi divide at the end of the trachea into the left and right main bronchi and these respectively divide into bronchial branches, which "feed" the three lobes of the lung on the right and two on the left. These bronchi continue to subdivide into bronchioles (smaller bronchi), over twenty three times in total. The over 100,000 bronchioles get smaller in diameter and ultimately terminate in over 300 million air sacs, called alveoli. The alveoli, which are clustered like grapes, are approximately 0.3 mm in diameter and provide a huge surface area for gas exchange to take place. There are capillaries surrounding the alveoli and this is where the inspired oxygen is diffused into the vascular system of the body. Likewise, toxic $CO_2$ is diffused into the alveoli from the capillaries and is removed from the body during expiration.

With no external loads, the lung structure is approximately the size of a grapefruit. It is expanded larger in the chest cavity with a physiologic level of vacuum that stretches it to the chest wall. As we inhale, we are forcing the lung cavity to a larger condition by flexing the ribs and lowering the diaphragm. The vacuum around the lungs pull the lung volume larger as the chest volume is increased; air pressure in the lung is reduced and atmospheric air pressure forces air into the lung. During expiration, the diaphragm and ribs are relaxed to allow the elastic properties of the lung to pull the chest cavity to a smaller volume and to force air out of the lungs.

Chronic Obstructive Pulmonary Disease ("COPD") is a progressive disease that causes lung parenchyma to lose elastic properties and lose surface area that is required to exchange gas such as $O_2$ and $CO_2$. Lung tissue is eroded to leave large holes, typically in the upper lobes. The holes do not contribute to the elastic pulling forces required during expiration. Areas adjacent to the holes are more highly stressed. The stressed tissue stretches and loses recoil properties. These stretched regions fail to pull on and thus fail to suspend the major airways in a radial fashion to hold them open. As the disease progresses, the patient will eventually need to force expiration, which causes the major airways to collapse and block air flow. This effect is exacerbated with additional applied expiration pressure since the airways are ill-supported. During inspiration, these unsupported regions fill preferentially since they are floppy and have no resistance to expand (no elasticity). They preferentially consume the oxygenated air even though there is little remaining surface area to exchange $O_2$ to the bloodstream.

Normal lungs rarely present with collateral flow paths between lobules and between major lobes of the lung in the form of pores and leak paths. In COPD patients, damaged tissue forms vacuoles or holes, which grow in size (e.g., 2 µm to over 500 µm) and multiply to allow flow from numerous airway paths to supply these regions with air. As this tissue degradation occurs, numerous holes communicate with each other, and eventually the lobes communicate with each other, through means other than the normal airways.

Lung volume reduction surgery (LVRS) is a procedure where the chest is opened and a target region of lung is cut out. This accomplishes several things. It removes damaged regions that contribute very little to gas exchange. More importantly, it removes lung volume so that the healthy portion of the lung that remains can be expanded beyond typical physiologic volume (expand healthy functioning alveoli) to fill the chest cavity with functioning lung. The procedure increases surface area of healthy tissue to increase gas exchange. It also stretches the remaining tissue to restore support of the major airways, and it improves expiration mechanics. The procedure also cuts off blood circulation through the removed regions that had little effective gas exchange. This prevents $CO_2$ laden blood from mixing back into the left side of the heart and to the arteries.

While the LVRS procedure is ideal in many ways, it requires major chest intervention that requires cutting the chest plate or major spreading of ribs. Pain associated with this causes interruption of normal breathing and difficulty to revive the patient from forced ventilation to normal breathing after the procedure. The procedure presents with high mortality rates and long recovery times.

Another risk with LVRS is associated with cutting too much volume out. By cutting more than approximately one third of the expanded lung volume per side (one third of the chest cavity volume per side), the tissue may be over-stressed and rupture with expansion. These ruptures culminate as spontaneous pneumothorax events (leaks that vent vacuum holding the lung up to the chest wall and allow collapse of the lung). Also, adhesions between the lung and chest wall that occur naturally present stress points upon expansion that can cause ruptures.

Tension pneumothorax complications can also be caused by the surgery. This is a condition that causes central chest organs to shift. The imbalance of force in the chest after expanding highly elastic lung tissue pulls the mediastinal region of the central thorax sufficiently to actually shift large vessels and cause flow restrictions. This condition can be very serious and warrant further surgeries.

If lung volume reduction ("LVR") could be accomplished less invasively, the complications and morbidity associated with the surgery could be nearly eliminated. In addition, the procedure would be open to many more patients who might not be able to or not desire to undergo a major thoracic surgical procedure. Current less invasive approaches to LVR have met with limited success, however.

Bronchoscopically-placed LVR devices have been described which may be implanted into the lungs to block airways in an attempt to create a volume reduction effect distal to the blocking device to emulate LVRS. For example, plug and one-way air directing devices are introduced to block an area of the lung to cause oxygen depletion distally to cause volume reduction through a process known as atelectasis. These devices may provide some relief to the patient by blocking preferential filling of damaged lung tissue. All of these devices are inserted through the working channel of a flexible bronchoscope and are placed only as far as the third to the fifth subdivision or segment of bronchi.

However, there are several problems with these earlier devices as they are currently used. Current blocking devices do not facilitate access to distal regions of the lung after deployment to allow for reoccurring interventions or treatments.

In addition, current bronchoscope working channels are typically 2.0 mm in diameter; the blocking and one—way valve devices must be expanded to seat in airways that are as large as 15 mm in diameter. Therefore, the expansion ratio for these devices needs to sometimes be as high as 750%. Covered devices that are stretched to this extent are typically not robust air leak seals. Current devices are made small enough to fit down the working channel of the bronchoscope so they can be pushed out to self deploy. The devices are typically made of Nitinol alloys with long elastic range that drives recovery to an expanded state. This also requires that the device be scaled down to such a small diameter profile that the self expansion forces are extremely low to anchor the device and the covering materials must be thin and therefore fragile.

Moreover, these devices block air from flowing in the major airways but are not effective if collateral flow paths exist. The collateral paths allow the distal region to fill and hyper-inflate. When collateral flow is not an issue, these devices block $O_2$ and $CO_2$ exchange, and yet the blood flow in the region still carries $CO_2$ laden blood through the lungs to mix with systemic blood flow. Finally, uncontrolled atelectasis beyond a one third volume reduction may cause tension pneumothorax complications and stress ruptures within the lung wall, causing lung collapse.

SUMMARY OF THE INVENTION

The invention provides methods of performing lung volume reduction to treat a patient. One aspect of the invention provides a method of compressing a first portion of a lung of a patient including the following steps: providing a vent connecting the first portion of the lung to the exterior of the patient; isolating the first portion of the lung from a second portion of the lung adjacent the first portion; and delivering pressurized fluid to the second portion of the lung to compress the first portion of the lung. In some embodiments, the isolating step includes the step of delivering an expandable device to an air passageway communicating with and proximal to the first portion of the lung, with the step of providing a vent in some cases including the step venting the expandable device. In some embodiments, the isolating step includes the step of delivering a plurality of expandable devices to air passageways communicating with and proximal to the first portion of the lung.

In some embodiments of the invention, the step of delivering pressurized fluid includes the step of delivering pressurized fluid at a pressure of at least 10 mm Hg, 25 mm Hg, 45 mm Hg, or 55 mm Hg above atmospheric pressure. Some embodiments include the step of permitting fluid to enter the first lung portion when a difference between fluid pressure within the first lung portion and fluid pressure in the second lung portion exceeds about 2 mm Hg, about 10 mm Hg, about 20 mm Hg or about 50 mm Hg.

Another aspect of the invention provides a method of collapsing a portion of a lung of a patient including the following steps: inserting a catheter into the lung portion; and venting the lung portion through the catheter to the exterior of the patient without aspiration.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 is a cross-sectional view of an intra-bronchial device and deployment system according to yet another embodiment of the invention.

FIG. 6 shows the use of an intra-bronchial device to treat a patient.

FIG. 7 shows yet another intra-bronchial device implanted in a patient's lung.

FIG. 8 shows an agent dispensing mechanism for possible use with this invention.

FIG. 14 is a cross-sectional view of still embodiment of an intra-bronchial device and delivery mechanism with a tool passing through the device's plug.

FIG. 15 is a schematic view of the plug of the device of FIG. 14 in a closed position.

FIG. 16 is a schematic view of the plug of the device of FIG. 14 in an open position.

DETAILED DESCRIPTION OF THE INVENTION

Figure 1:
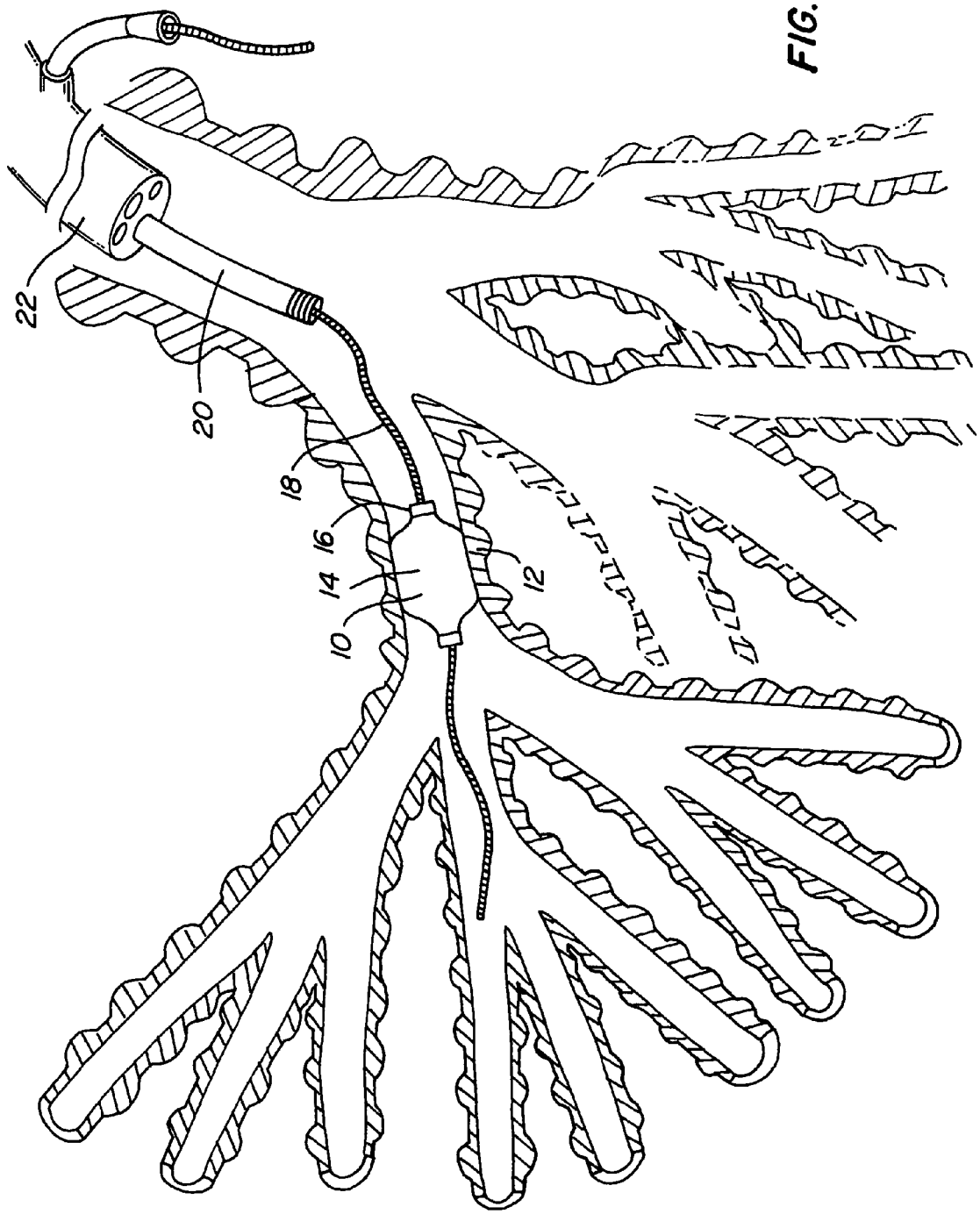
FIG. 1 is a perspective view of an intra-bronchial device and delivery system according to one embodiment disposed within a patient's lung.

The following tools may be used to treat COPD patients in a minimally invasive manner: Imaging and embolic devices to block blood flow through the target lung tissue; devices to help prepare the lung for devices and agents; a side wire delivery system that is advanced alongside the bronchoscope to guide and release several implants without removing the scope; a lung volume reduction implant device (Intra-Bronchial Device or IBD) that is controllably coupled to a delivery catheter that includes a working channel that runs through the center of the catheter and the implant; an inflator catheter that fits down the middle of the IBD and delivery catheter to inflate the IBD; an IBD plug element and delivery system; a deflation device to reposition or remove the IBD; a collateral flow detecting device; collateral flow blocking agents; adhesion promoting agents to maintain atelectasis; and a lung tissue compressing system. These items provide a reliable minimally invasive procedure for COPD patients and enable follow-on procedures to maintain a high degree of restored lung mechanics and gas exchange without causing tissue stress or blood chemistry complications that occur with current technology.

Perfusion of air flow in the lungs can be imaged using MRI imaging equipment while the patient breathes water saturated air or agents that are comprised primarily of water. Moving water molecules produce a strong signal, whereas static air and water will not produce a signal. This distinction is important to determine where the degraded lung hole regions reside. Hyper-polarized gases such as helium, helium-3 and xenon-129 also work extremely well in the lung to find damaged tissue and identify collateral flow. Computed tomography has also worked very well to identify damaged tissue in lungs. These imaging modalities can be used in real time before, after or during the procedure to check the patient's condition. They can also be used to guide intervention in an iterative fashion between imaging sessions or in real time. Ventilation Scans via SPECT (Xe-133) may also be used.

Specially-designed catheters can introduce lavage agents to the lung to wash mucus and surfactants. Mucus and naturally occurring surfactants trap solids and agents to block collateral flow paths and promote adhesions within the targeted lung region or portion. Cleaning these regions to remove fluids, mucus and surfactants improves distribution of these agents and enhances adhesion of glue compositions that may be infused into the region.

Fluoroscopic x-ray imaging is very useful to determine where blood flows through COPD damaged lung tissue. By introducing radiopaque high contrast materials into the blood stream, and with the use of digital subtraction techniques, the flow paths can be imaged very clearly. Embolic devices and agents that are used to treat peripheral vasculature may be utilized to embolize the pulmonary veins and arteries that normally exchange gases through the regions of the lung that are going to be or have been blocked and treated by the devices and agents of this invention. Exemplary embolic devices include embolic polymeric implants such as Dacron fibers, metallic coils, alcohols, glutaraldehyde, gels, foams, and glue such as cyanoacrylates, PEG based glues and glutaraldehyde based glues.

Embolizing this pulmonary vasculature will reduce or prevent $CO_2$ mixing into the heart. Pressure probes such as piezo, thermal transfer flow wires or micro-electrical-mechanical system (MEMS) wave interference pressure and flow transducers may be introduced or implanted to monitor pulmonary hypertension as the blood flow paths are being blocked and to monitor results over a period of time. That way the procedure can be limited to prevent undue blood back pressure on the heart. The lung tissue in the region will still be supplied with oxygenated blood from a separate artery system that feeds pulmonary tissue. Implantable MEMS devices can be used to measure pressure, temperature, strain and stress on tissues that are affected by the lung volume reduction procedure. MEMS transducers are passive (no electronics or batteries on board) implantable devices that can be queried using magnetic wave transmitter/receiver probes outside the body.

The design of the current invention resolves most of the deficiencies and issues related to the devices described above. The intra-bronchial device is placed in segments of bronchi that feed the diseased areas of the lung. As many as five to ten intra-bronchial devices could be placed in the bronchi of any one patient. The goal is to cause atelectasis in these areas and cumulatively expand the healthy portions of the lung, thereby replicating the results and benefits of LVRS, but without the morbidity and mortality.

FIG. 1 shows an intra-bronchial device 10 according to one embodiment of this invention disposed within a bronchial tube 12 of a patient's lung. Device 10 is in contact with the inner wall of bronchial tube 12 and is preferably immobilized through a friction fit. In this embodiment, device 10 includes an expandable balloon 14 with a central lumen 16 through which other devices or tools (such as guidewire 18, as shown) may be passed. Device 10 may be delivered and deployed via a catheter 20 disposed within a working channel of a bronchoscope 22.

Figure 2:
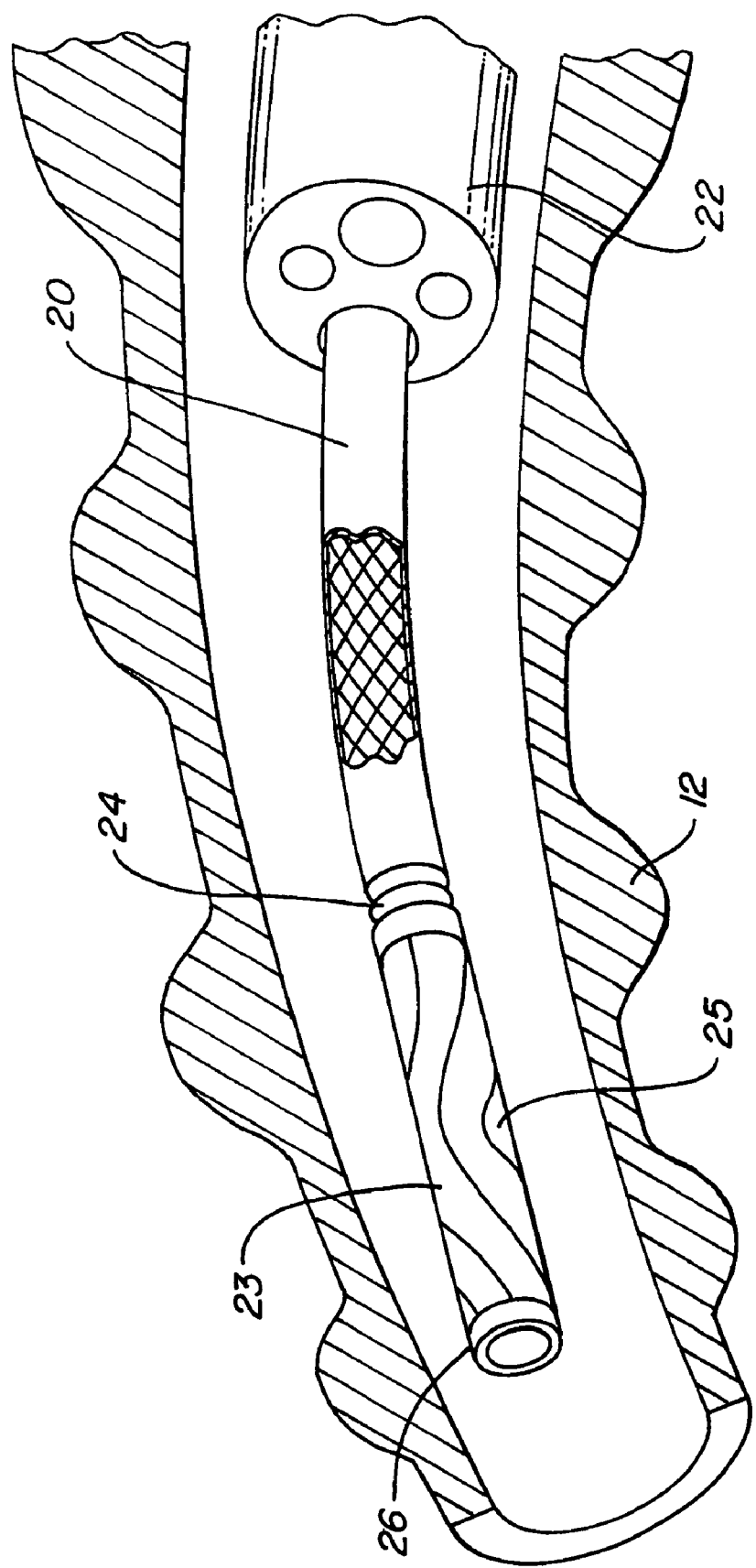
FIG. 2 is a detail view of an intra-bronchial device and delivery system according to another embodiment of the invention.

FIG. 2 shows details of another embodiment of the invention. Device 23 may be delivered and deployed via a catheter 20 disposed within a working channel of a bronchoscope 22. Delivery catheter 20 is connected to an inflatable balloon 25 of device 23 via a coupler 24 that may be connected and disconnected as desired. In this embodiment, catheter 20 has a braided shaft, and balloon 25 is a folded semi-elastic balloon made from polyethylene, polyvinyl, latex, etc. (Polyethylene is particularly preferable due to the its tissue ingrowth inhibition properties.) Balloon 25 may also be a uniform elastic balloon made from, e.g., silicone or polyurethane. The device has a ring 26 (made, e.g., from nitinol, stainless steel, polymer, Teflon, ceramic, composites, high density polyethylene, low density polyethylene, nylon, polyurethane) at its distal end marking the outlet of the balloon's central lumen. Catheter 20 may be used to deliver the device to a target site within the patient's bronchial tube 12 and/or to inflate balloon 25 once at the target site.

Figure 3:
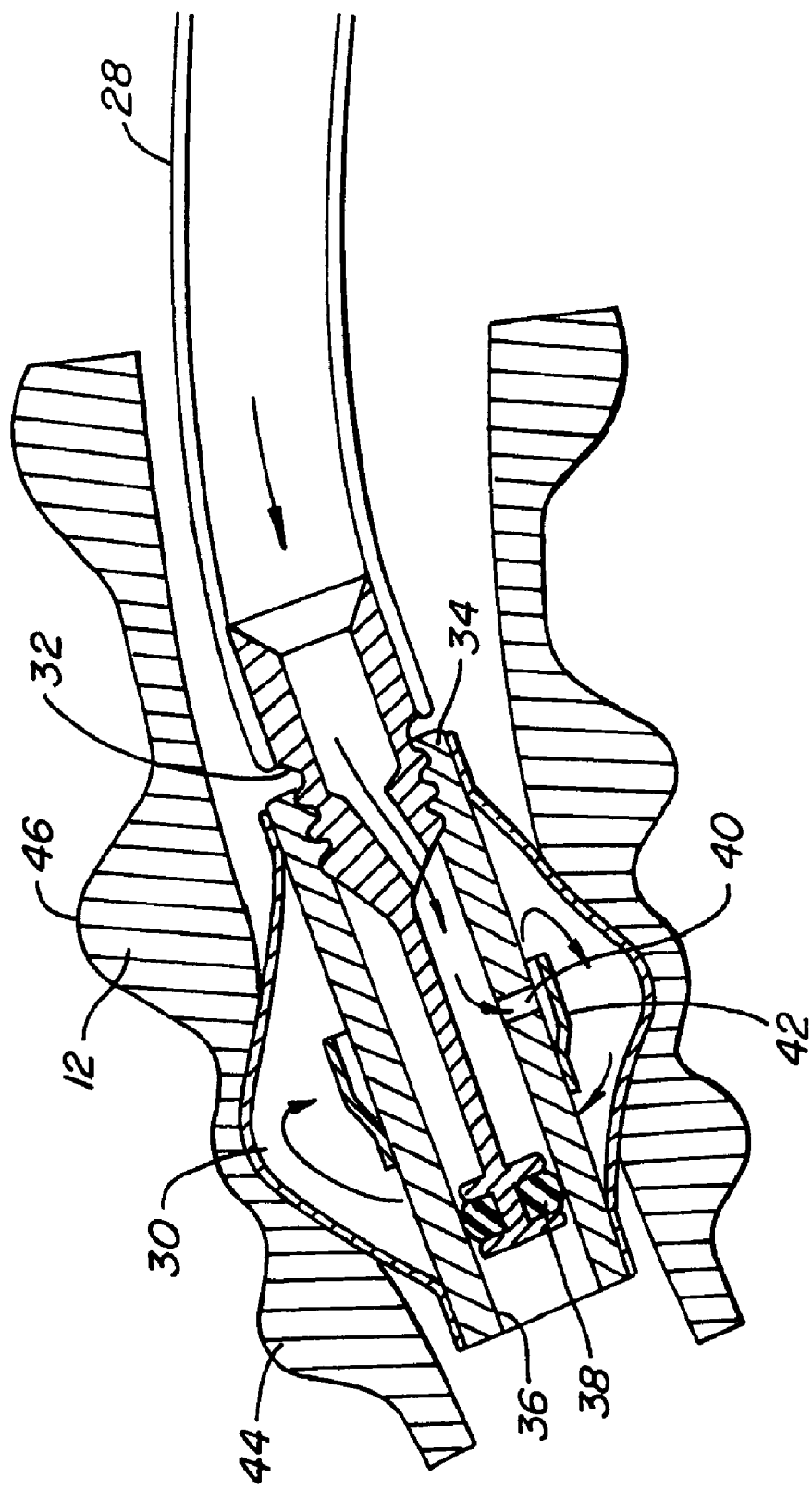
FIG. 3 is a cross-sectional view of an intra-bronchial device and deployment system according to yet another embodiment of the invention.

FIG. 3 shows one embodiment of a balloon deployment mechanism. In this embodiment, catheter 28 is coupled to balloon 30 via a threaded coupler 32 cooperating with internal threads 34 within the central lumen 36 of balloon 30. Once in place at the target site, a fluid (such as a hydrogel, silicone, water, saline solution, air, glue, multipart catalytic solutions, fluidized metal, suspended metal, fluoroscopic contrast medium, sodium HA) can be injected through catheter 28 into lumen 36. A seal 38 at the distal end of coupler 32 prevents the injection fluid from passing through the distal end of balloon lumen 36. Instead, the fluid passes through one or more ports 40 in the wall of lumen 36 into balloon 30 to inflate the balloon. A one way flap 42 prevents the fluid from passing back into lumen 36 once the injection fluid pressure source is removed. After inflation of the balloon, catheter 28 may be rotated to disengage coupler 32 and to remove coupler 32 and seal 38 from the balloon. As shown in FIG. 3, the target site for the balloon is a bronchial wall site between adjacent cartilage areas 44 and 46, enabling the inflation of balloon 30 to distend the bronchial wall to enhance the balloon's grip on the wall.

Figure 4:
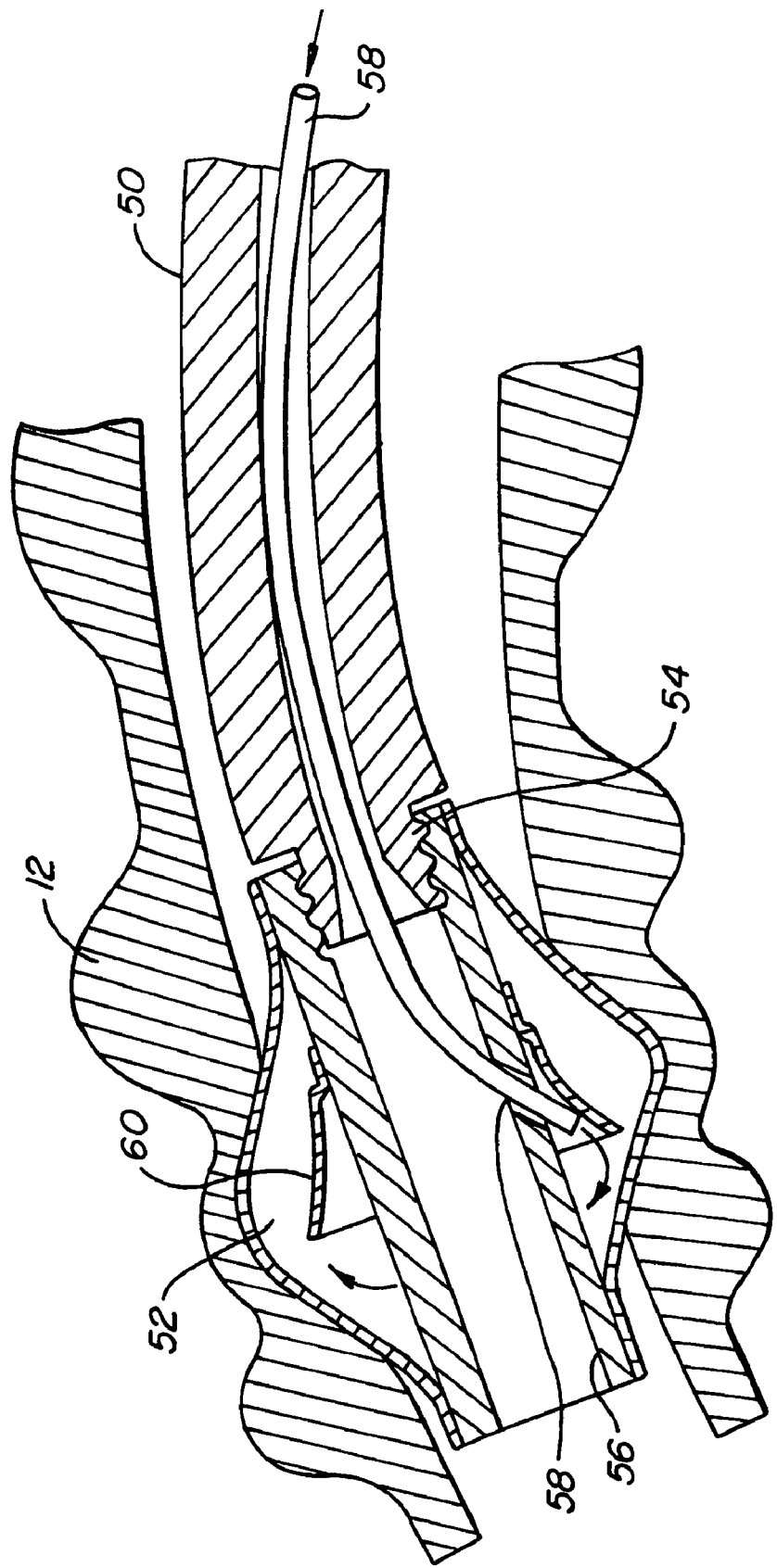
FIG. 4 is a cross-sectional view of an intra-bronchial device and deployment system according to still another embodiment of the invention.

FIG. 4 shows an alternative balloon deployment mechanism. In this embodiment, a catheter 50 is coupled to balloon 52 via a threaded coupler 54 cooperating with internal threads within the central lumen 56 of the balloon. A filler tube 58 extends through catheter 50 into lumen 56 and through a port 58 formed in the lumen wall to push open a flap 60 to communicate filler tube 58 with the inside of balloon 52. Filler tube 58 may be used to inflate the balloon with an injection fluid, such as one of the fluids listed above. Filler tube 58 may also be used to remove fluid from the balloon to deflate the balloon for removal or repositioning of the balloon. After inflation of the balloon, catheter 50 may be rotated to disengage coupler 54 from balloon 52.

FIG. 5 shows yet another embodiment of the invention. In this embodiment, balloon 70 is inflated so that it does not substantially distend the bronchial tube walls. Balloon 70 is also longer than the balloons of the previous embodiments, extending, e.g., beyond adjacent cartilage sections of the bronchial tube wall. The balloon's configuration allows it to distort as the bronchial expands and contracts during the patient's breathing cycle.

Balloon 70 may be inflated using, e.g., the balloon deployment mechanisms described above with respect to FIGS. 3 and 4. A port 72 communicates the device's inner lumen 73 with the inside of the balloon through a flap 74, as described above.

FIG. 5 also shows yet another mechanism for releasably coupling a catheter to the device. Catheter 76 has a split distal end 78 with an annular engagement structure 80 configured to engage with an annular channel 82 formed on the proximal end of the device. A coupler sleeve 84 surrounding catheter 76 may be retracted proximally to permit the split distal end 78 to expand outwardly, thereby disengaging the device, and may be advanced distally to pull distal end 78 radially inward to engage the device.

FIG. 6 shows the use of an intra-bronchial device to treat a patient. An expandable intra-bronchial device 100 (such as one of the balloon devices described above) has been deployed at a target site in a patient's bronchial tube 102 via, e.g., a delivery catheter 104. A second catheter 106 has been passed through catheter 104 and the central lumen of device 100 to a treatment site 108 further down into the patient's lung. The distal end 110 of catheter 106 may be lodged in the patient's bronchial at the treatment site. Catheter 106 may then be used to induce atelectasis via, e.g., suction, vacuum, lavage with an anti-surfactant agent, mechanical compression, sclerosing agents (such as alcohol or other fluids or aerosols), etc.

FIG. 7 shows the use of an intra-bronchial device to treat a patient in another manner. An expandable intra-bronchial device 120 (such as one of the balloon devices described above) has been deployed at a target site in a patient's bronchial tube 122. A plurality of wires 124 are delivered through the central lumen of device 120 to place the wires' distal ends 126 within a lobe or section 128 of the patient's lung. The wire ends are glued or anchored to the tissue within lobe 128. The proximal ends of wires 124 have one-way locks 130 that may be pulled proximally through the device's 120 central lumen after anchoring of the distal ends to collapse lobe 128 inwardly. Locks 130 hold wires 124 in position, as shown.

FIG. 8 shows an agent-dispensing mechanism for possible use with this invention. A delivery catheter 131 is mounted on a guidewire 132 via a sideport 133. Agents such as glue or other substances may be delivered from syringe 134 via catheter 131 through an intra-bronchial device to the lung region distal to the intra-bronchial device. (The length of catheter 131 is shortened in FIG. 8 for illustration purposes. The catheter must be long enough for the syringe to be outside the patient's body and the distal end of the syringe extending into and through the intra-bronchial device.)

Figure 9:
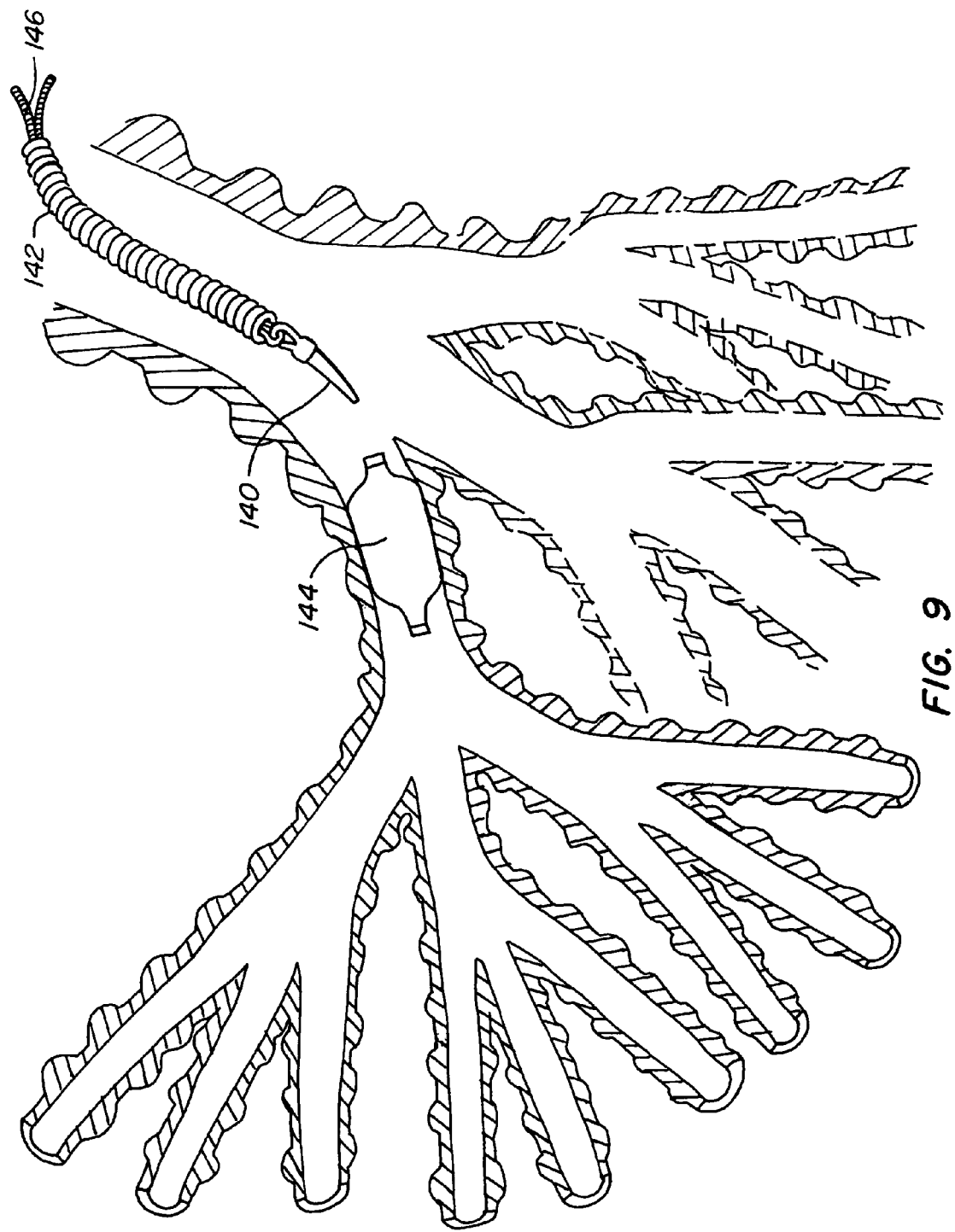
FIG. 9 shows a plug and delivery mechanism for use with an intra-bronchial device.

After treatment of lung tissue distal to an intra-bronchial device, the device's central lumen may be closed. The device's central lumen may thereafter be opened should access to lung tissue distal to the device be desired. FIG. 9 shows one embodiment of an intra-bronchial device plug 140 for deployment via catheter 142 to seal device 144 (such as one of the balloon devices described above). A tether 146 may be used to disengage plug 140 after deployment in device 144.

Figure 10:
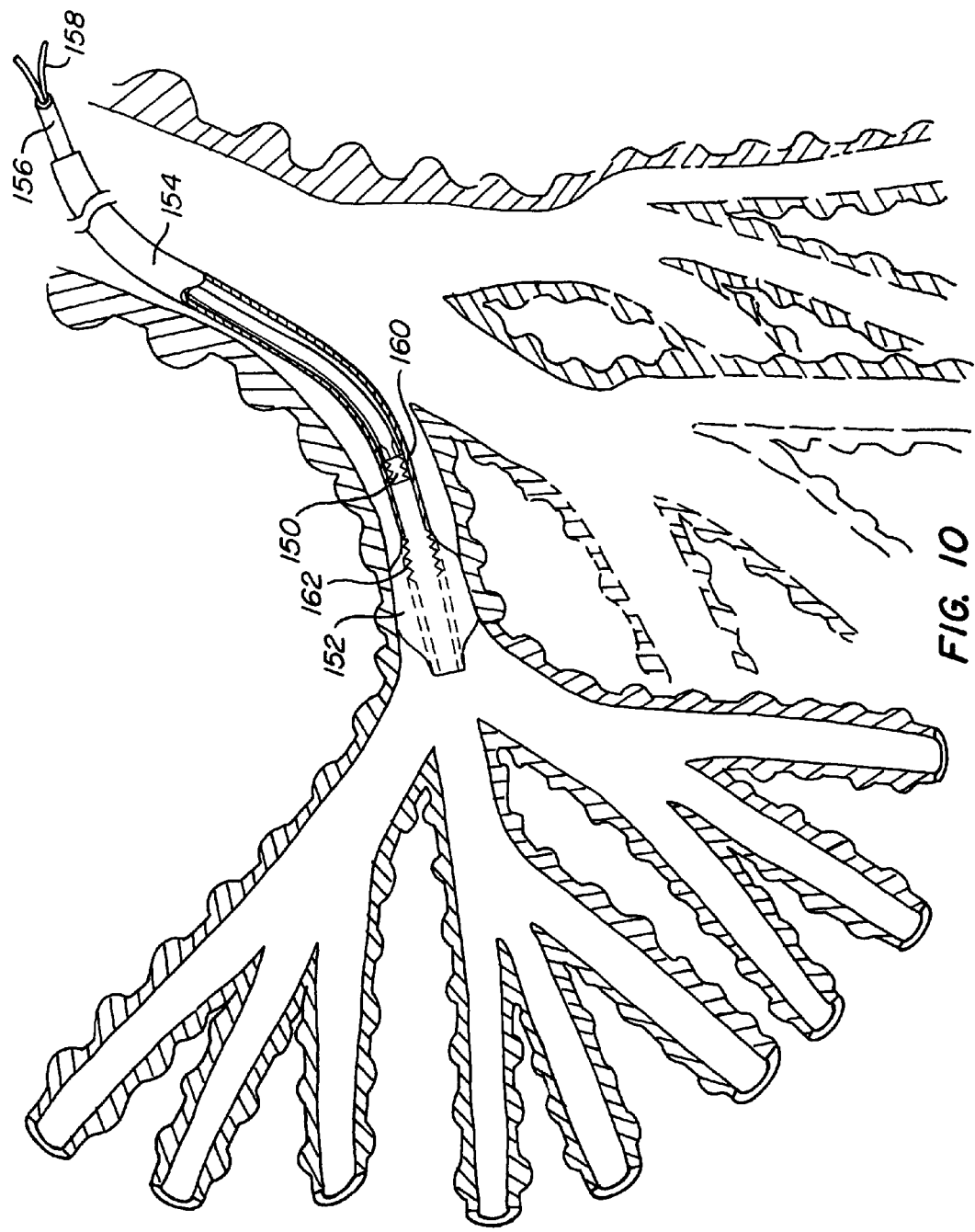
FIG. 10 is partial cross-sectional view of a plug and delivery mechanism for use with an intra-bronchial device.
Figure 11:
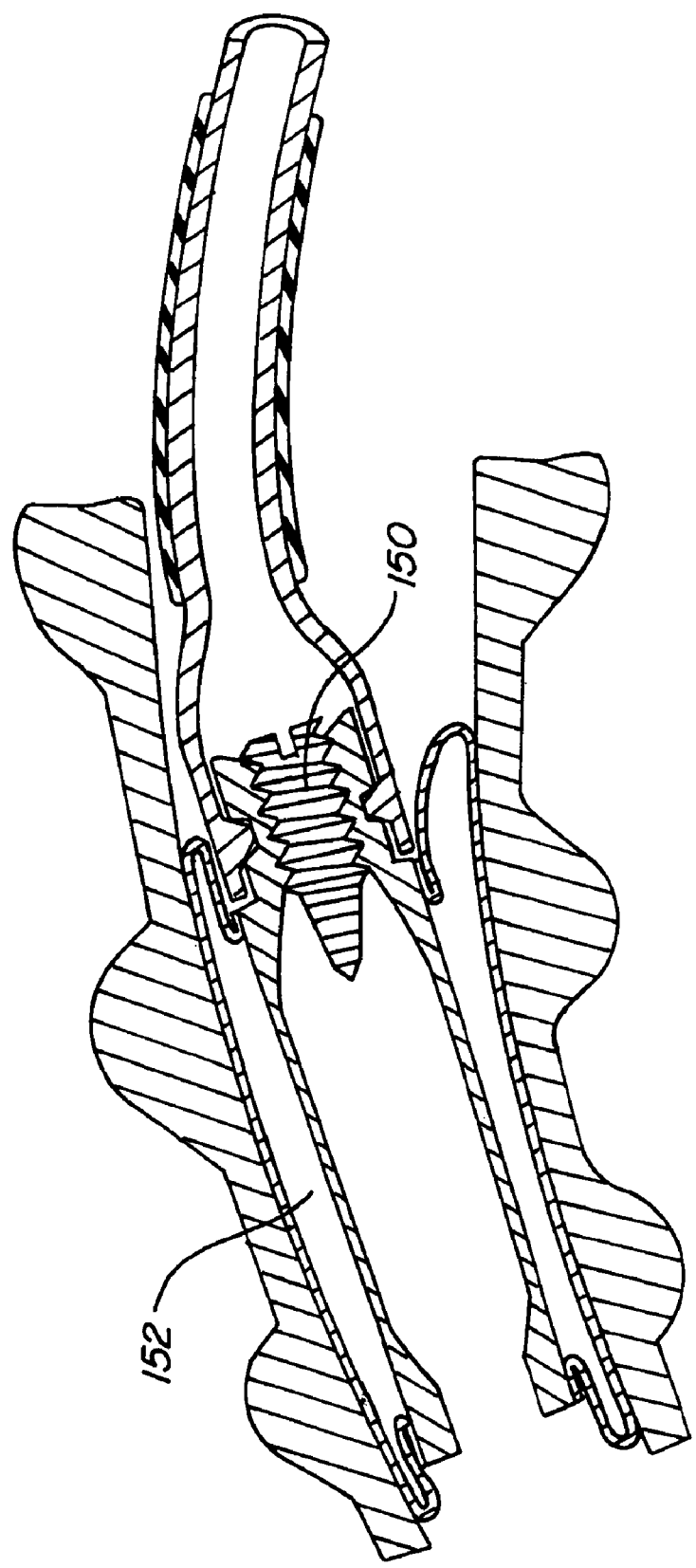
FIG. 11 is a cross-sectional view of the intra-bronchial device of FIG. 10 showing the plug in place.

FIGS. 10 and 11 show another embodiment of an intra-bronchial device plug 150 being delivered to device 152 (such as one of the balloon devices described above) via delivery catheter 154. Plug 150 is releasably held to a plug pusher or catheter 156 by a tether 158. Plug 150 has threads 160 that engage with threads 162 in device 152 when plug 150 is rotated by catheter 156 to seal the central lumen of device 152.

Figure 12:
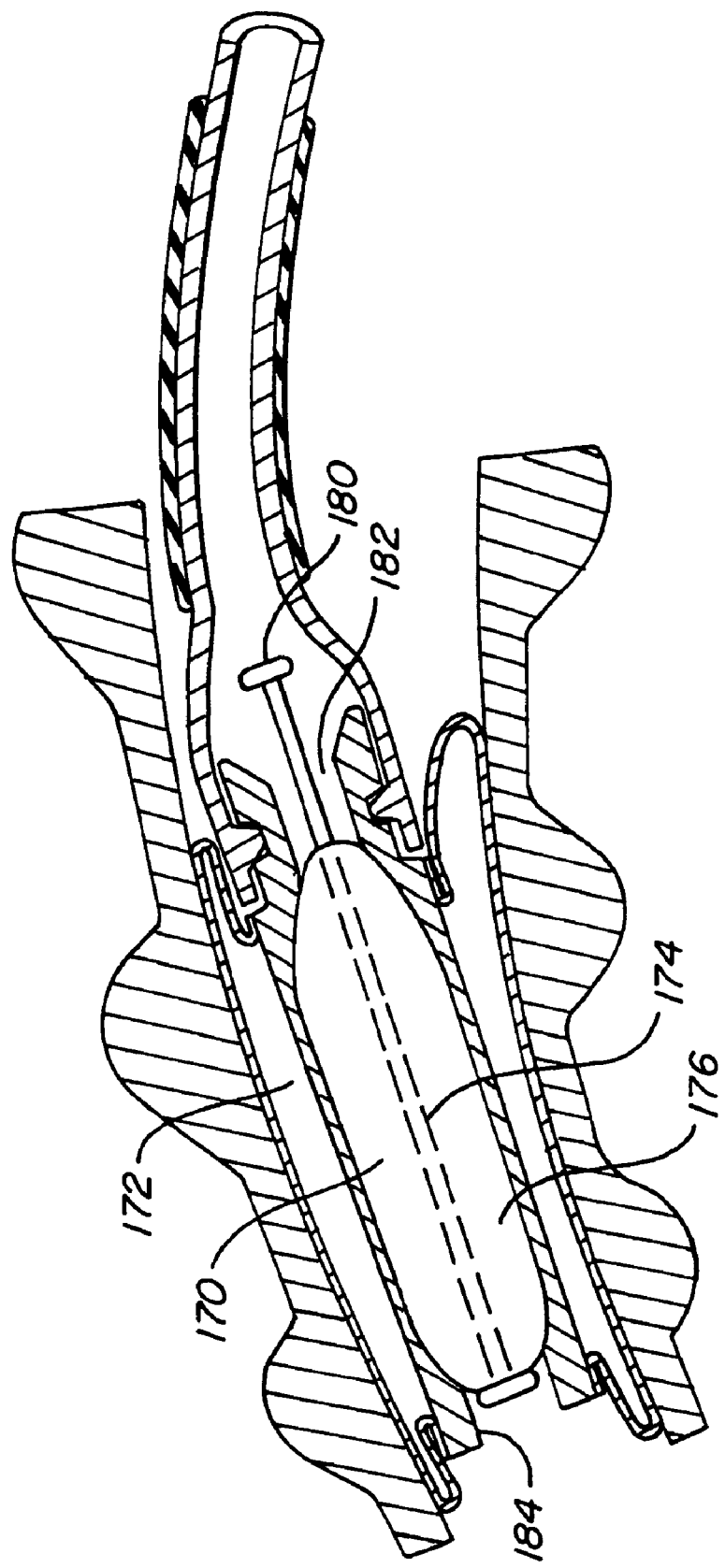
FIG. 12 is a cross-sectional view of another embodiment of an intra-bronchial device and delivery mechanism with a plug in place.

FIG. 12 shows yet another embodiment of a plug 170 for an intra-bronchial device 172 (such as the balloon device described above with respect to FIG. 5). Plug 170 has a stem 174 (formed, e.g., from metal or plastic) passing through an occlusion element 176 formed from an elastomeric polymer or gel. Plug 170 may be advanced into position by compressing it through a narrowed proximal end 182 of the central lumen 184 of device 172 through the action of a pusher or catheter (not shown) coupled to a coupling surface 180 formed on the proximal end of stem 174. To reopen the central lumen 184 of device 172, plug 170 may be advanced distally or retracted proximally.

In alternative embodiments, the plug may attach to the device using notches, luer locks, press fit, tapers, etc.

Figure 13:
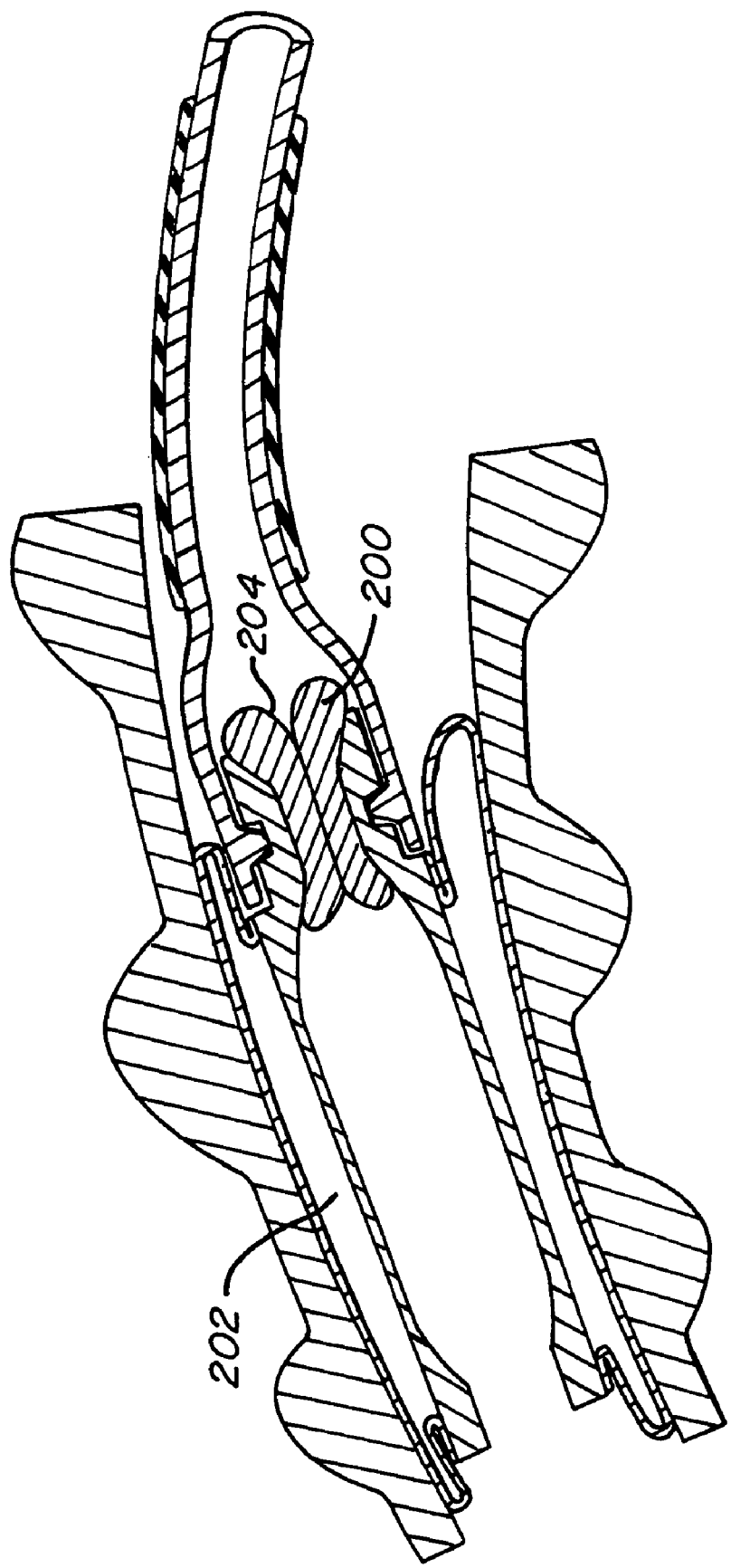
FIG. 13 is a cross-sectional view of yet embodiment of an intra-bronchial device and delivery mechanism.

FIG. 13 shows yet another plug 200 for an intra-bronchial device 202. In this embodiment, plug 200 forms an elastomeric seal around a central opening 204 through which tools or other devices may be inserted. Plug 200 may be integral with device 202 so that it does not have to be delivered separately from device 202.

FIGS. 14-16 show an intra-bronchial device 210 with an integral seal 212 having a central opening 213 formed by the cooperation of a plurality of flaps 216. Seal 212 may be integral with the central tube 214 of device 210. Central tube 214 and seal 212 may be formed from an elastic metal or polymer or rubber to allow flaps 216 to bend (as shown in FIG. 16) to permit devices or tools to be passed through opening 213. Flaps 216 return to their sealing position of FIG. 15 after the tool or device (such as guide wire 215) has been removed.

FIGS. 11-14 show plugged intra-bronchial devices attached to their respective catheters using releasable coupling mechanisms such as those described above with respect to FIG. 5. The coupling mechanisms help hold the device in place at the target site while the plug is being inserted.

It may also be necessary after deployment of an intra-bronchial device to deflate the balloon and remove the device from the patient. In addition to the deflation method described above with respect to FIG. 4, deflation may be accomplished by, e.g., puncturing the balloon. Once the balloon is deflated, the device may be coupled to a catheter as shown in FIGS. 11-14 and removed from the patient and/or deployed at a different site.

Figure 17:
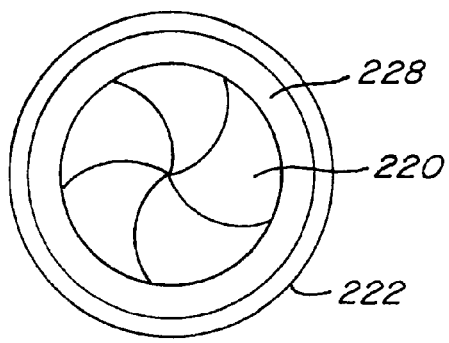
FIG. 17 shows another embodiment of an intra-bronchial device opening mechanism in a closed position.
Figure 18:
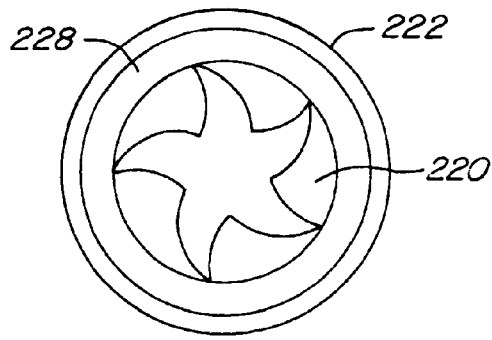
FIG. 18 shows the embodiment of FIG. 17 in an open position.
Figure 19:
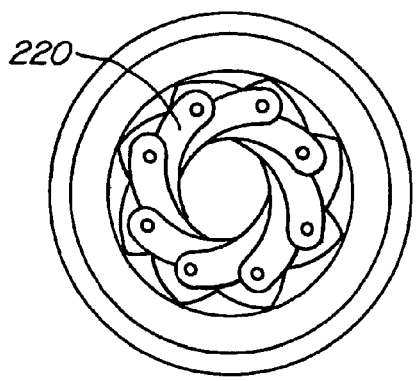
FIG. 19 is an elevational view another embodiment of an intra-bronchial device opening mechanism.
Figure 20:
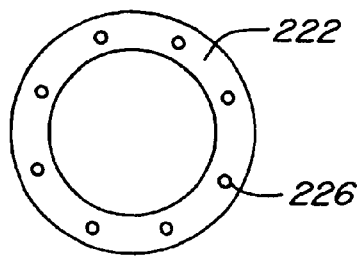
FIG. 20 is an elevational view of a ring for use with the mechanism of FIG. 19.
Figure 21:
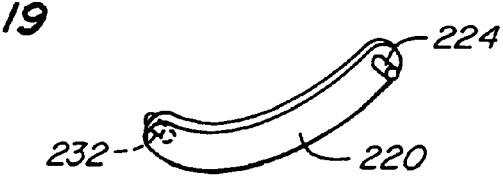
FIG. 21 is a perspective view of a blade for use with the mechanism of FIG. 19.
Figure 22:
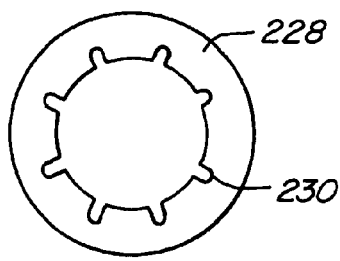
FIG. 22 is an elevational view of an actuating ring for use with the mechanism of FIG. 19.
Figure 23:
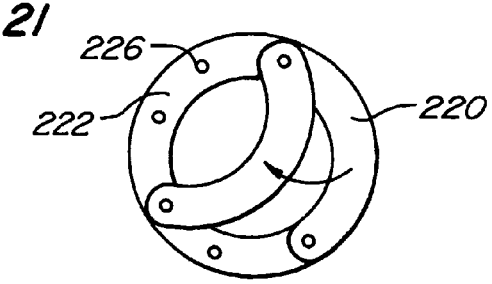
FIG. 23 shows the mechanism of FIG. 19, partially assembled.

FIGS. 17-23 show alternative designs for intra-bronchial device openings formed, e.g., as actuatable iris-type shutters. As shown in detail in the alternative embodiment of FIGS. 19-23, the shutter is formed from a plurality of blades 220 rotatably mounted on a ring 222 via pins 224 inserted into holes 226 formed in the ring. The blades are arranged in an overlapping arrangement as shown in FIG. 19. The shutter is operated by an actuating ring 228 having slots 230 interacting with a second set of pins 232 on blades 220. Rotation of ring 228 in one direction opens the shutter, and rotation of ring 228 in the other direction closes the shutter. FIGS. 17 and 18 show a five-blade shutter design, while FIGS. 19-23 show an eight-blade shutter design.

FIGS. 24-29 show another embodiment of the invention (outside of the lung, for ease of illustration). Intra-bronchial device 250 has a central shaft 252 surrounded by an expandable member, such as balloon 254. Shaft 252 has an opening 256 communicating the shaft's central lumen with the interior of balloon 254 via a flexible flap valve 258. Device 250 may be delivered to an air passageway of a patient's lung using a delivery catheter in, e.g., a manner described above.

Figure 24:
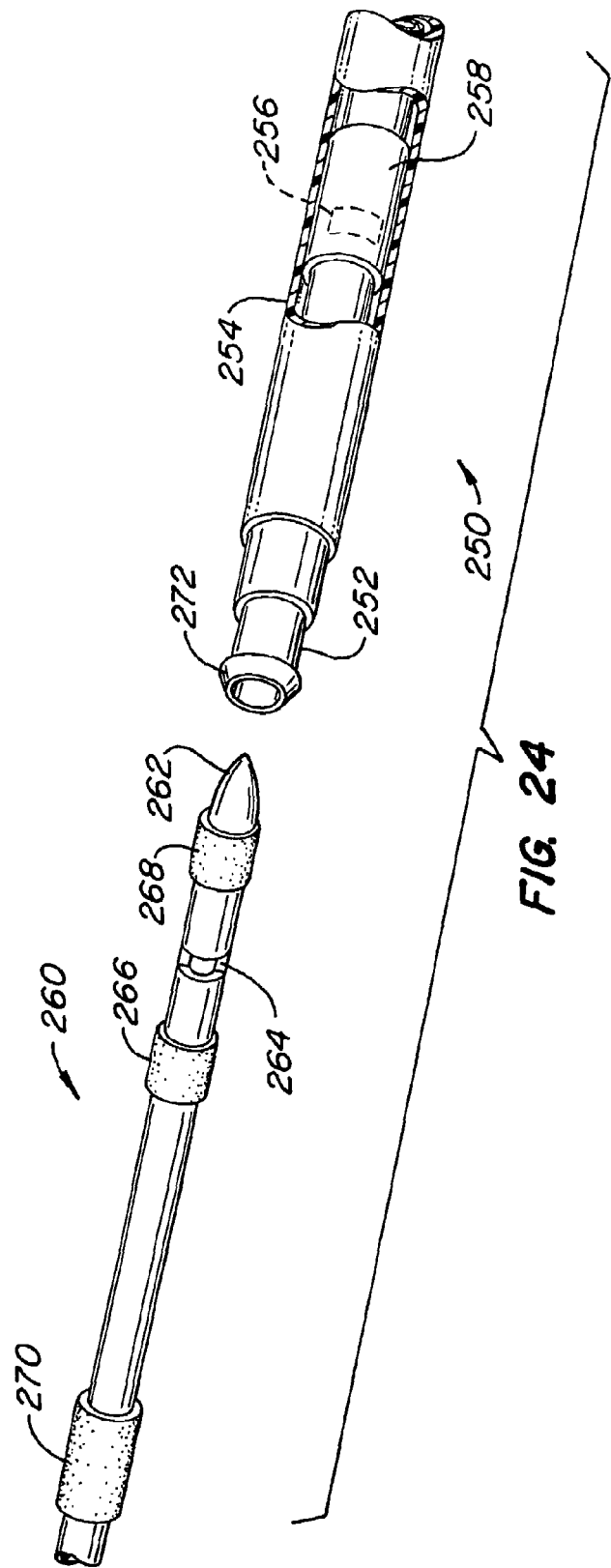
FIG. 24 is a partial perspective and partial cross-sectional view of yet another embodiment of an intra-bronchial device and deployment mechanism.
Figure 25:
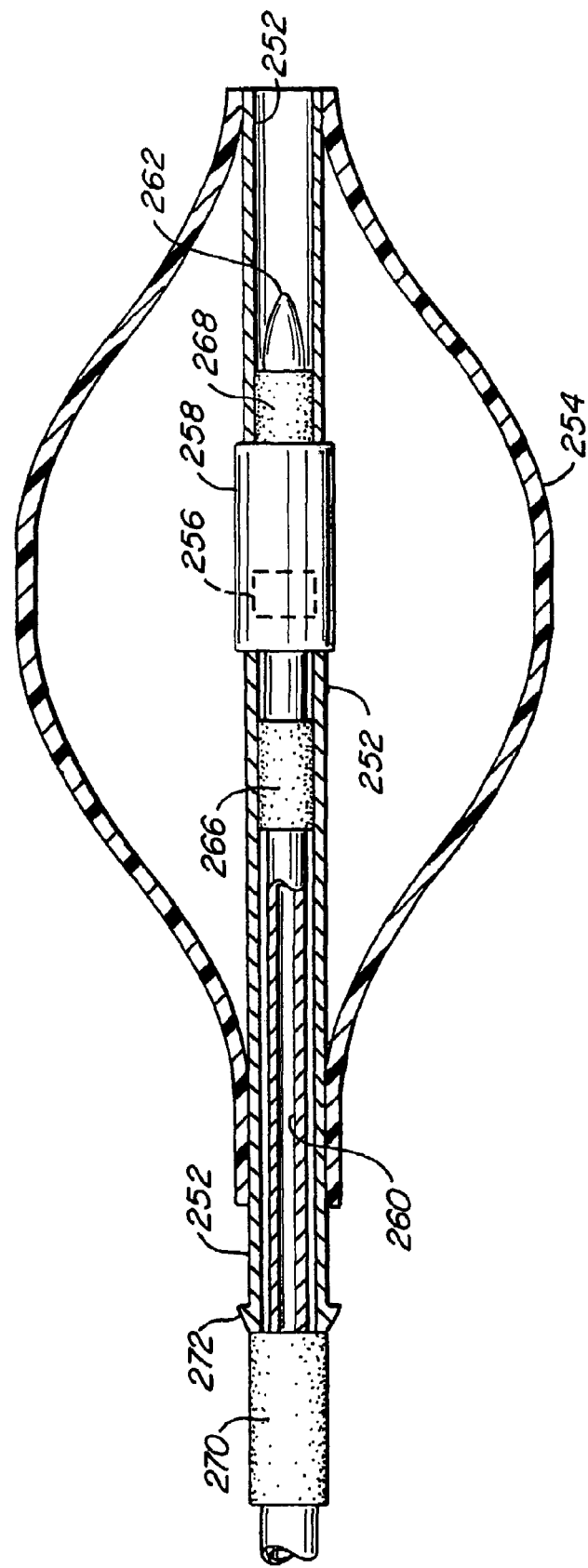
FIG. 25 is a cross-sectional view of the embodiment of FIG. 25 being expanded by the deployment mechanism.

An inflation catheter 260 may be used to inflate balloon 254 from the unexpanded condition shown in FIG. 24 to the expanded state of FIG. 25. Inflation catheter 260 may be inserted into the patient through the delivery catheter (delivered together with the device 250 or after it) or independent of the delivery catheter. The distal tip 262 of inflation catheter 260 has a pointed end to help align the inflation catheter with the intra-bronchial device's shaft. Inflation catheter 260 has an opening 264 with seals 266 and 268 on either side. When inserted into shaft 252, opening 264 aligns with the shaft's opening 256 when a shoulder 270 on inflation catheter 260 meets a shoulder 272 formed on the proximal end of device 250. Seals 266 and 268 ensure that pressurized fluid delivered to device 250 via inflation catheter 260 enters balloon 254 via openings 264 and 256 and flap valve 258 to inflate balloon 254. When the inflation pressure ceases, flap valve 258 closes to maintain balloon 254 in its inflated state. The device 250 may be inflated in multiple steps, as needed.

The inflation catheter may protrude through the distal end of the intra-bronchial device. By extending the inflation catheter tip length, we can provide a path to thread a delivery wire through the distal tip and out a side port to make the intra-bronchial device, intra-bronchial device delivery catheter and inflation catheter a rapid exchange system. Rapid exchange systems are catheter systems that can be threaded onto a short section of wire before the user can gain control of the wire end and the catheter system. By installing a catheter that does not provide a side port onto a wire, the user must advance the entire length of the catheter onto the wire before the user gains control of the end of the wire again. By providing a side port to any of the catheter devices required in the lung volume reduction kit, we enable the use of wires that are only long enough to extend outside the scope or patient and that provide for some extra length to be threaded into one or more devices and out the side port. Alternatively, the wire may be introduced into and out of a side port or it can be introduced in any combination of side, end or through lumen compartments.

Figure 26:
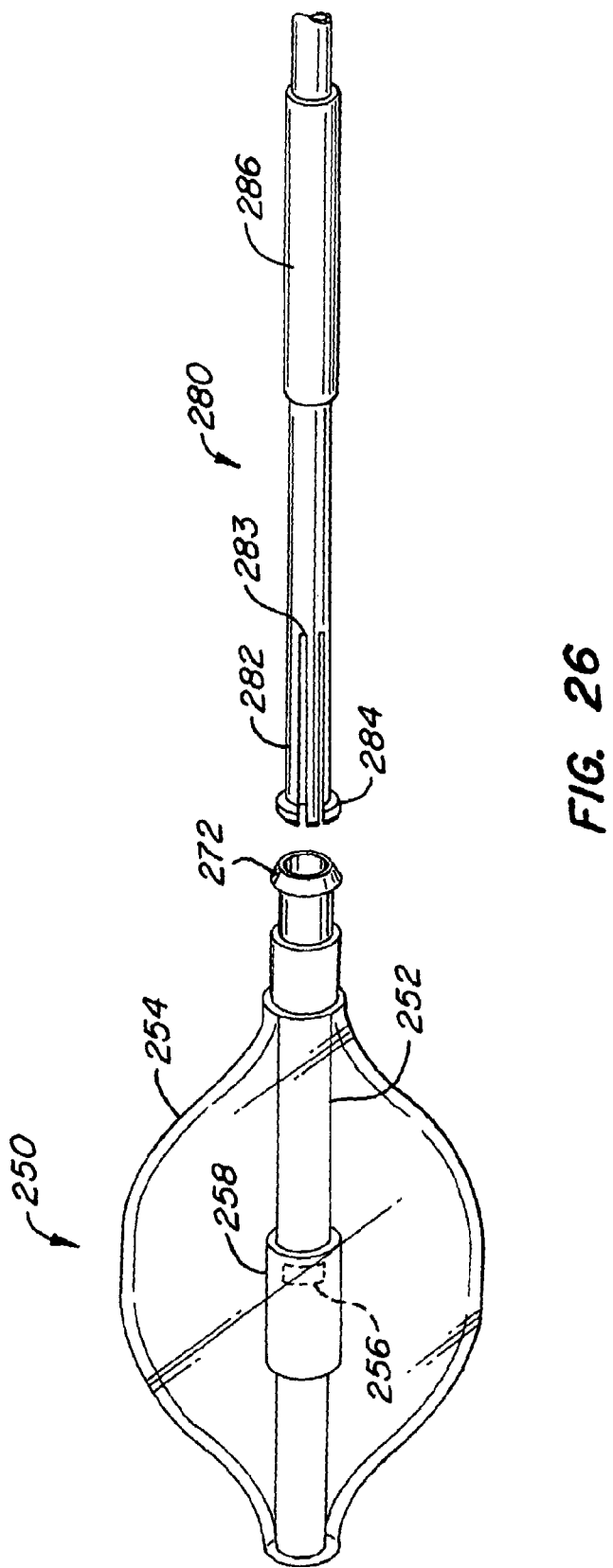
FIG. 26 is a perspective view of the intra-bronchial device of FIG. 24 and a deflation mechanism.
Figure 27:
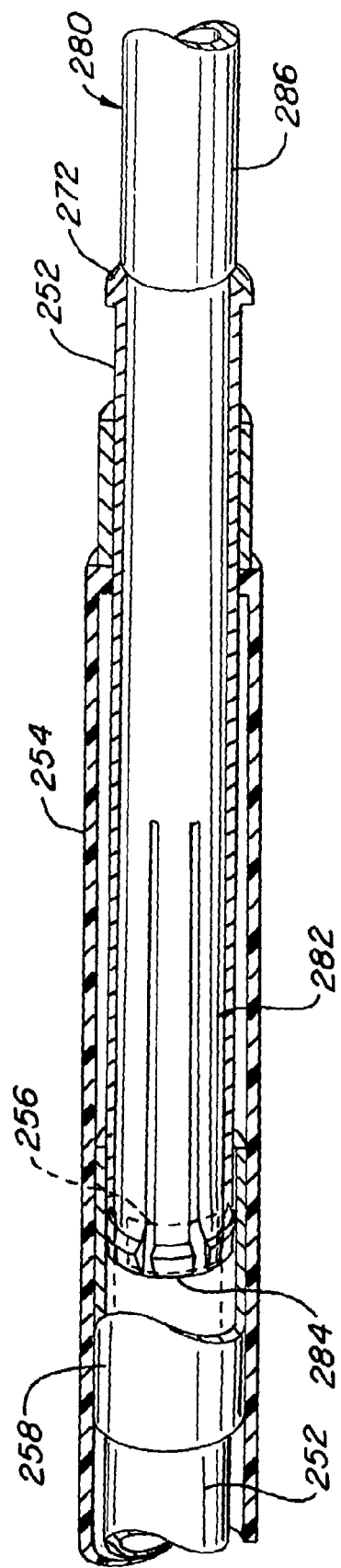
FIG. 27 is a cross-sectional view of the intra-bronchial device and deflation mechanism of FIG. 26.

FIGS. 26 and 27 show a deflation catheter 280 that may be used to deflate intra-bronchial device for removal or repositioning. Deflation catheter may be advanced through the device delivery catheter or independently. Deflation catheter has a plurality of fingers 282 separated by slots 283 and arranged circumferentially around the catheter's distal end. When advanced into shaft 252, shoulders 284 formed on the distal ends of fingers 282 cam radially inward to enable the catheter 280 to be advanced into device 250. When one or more shoulders 284 line up with opening 256 of device 250, their respective fingers move radially outward, displacing flap valve 258 away from opening 256 and permitting the balloon's inflation fluid to escape into catheter 280, thereby deflating balloon 254. A shoulder 286 meets shoulder 272 of device 250 when fingers 284 have been advanced distally to the proper position with respect to opening 256.

Figure 28:
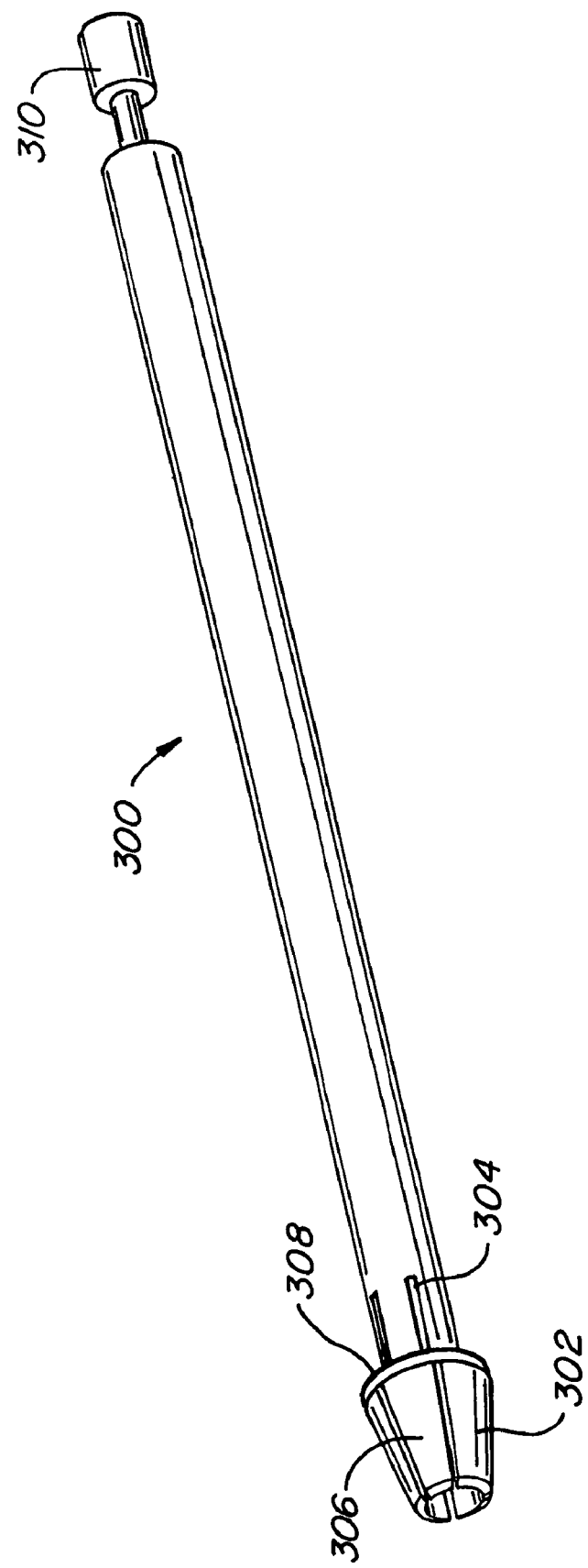
FIG. 28 is a perspective view of a plug for use with the intra-bronchial device of FIG. 24.
Figure 29:
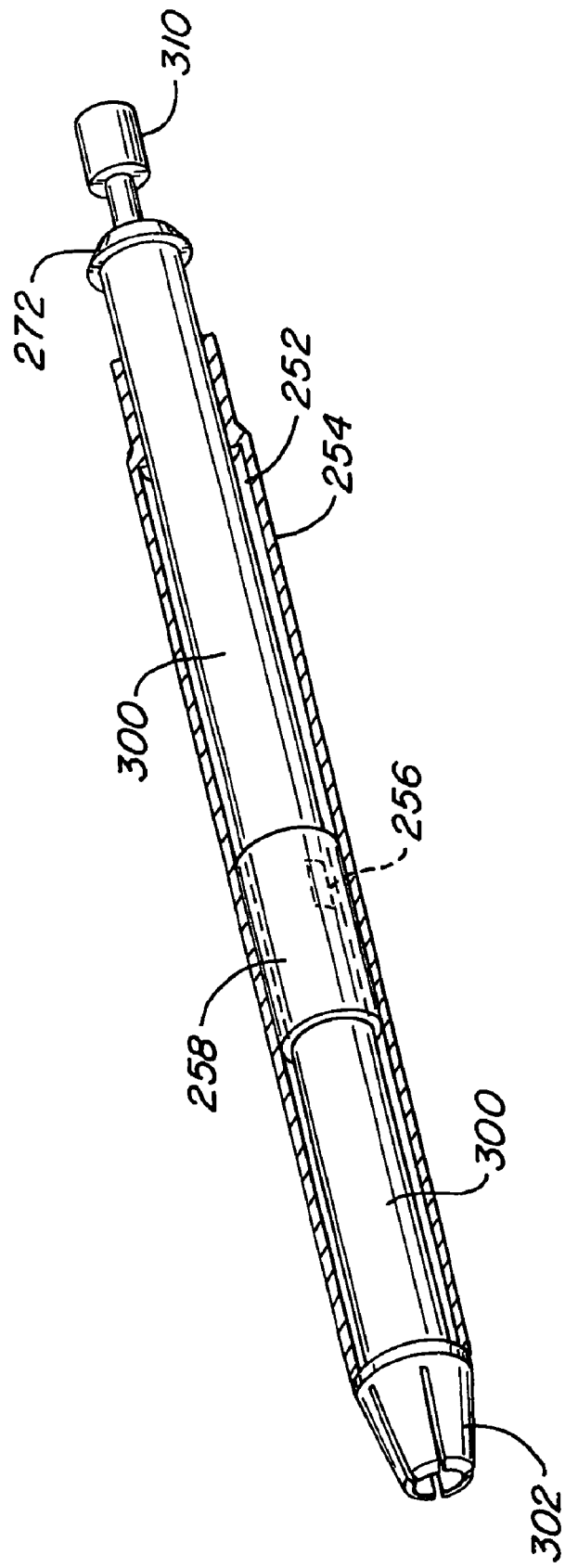
FIG. 29 shows the plug of FIG. 28 in place within an intra-bronchial device.

FIGS. 28 and 29 show a plug 300 for an intra-bronchial device, such as the device described in FIGS. 24 and 25. For illustration, FIG. 29 shows balloon 254 in a deflated state. A plurality of fingers 302 separated by slots 304 are disposed at the distal end of plug 300. The distal end of each finger 302 has an angled camming surface 306 facing distally and a steeper camming surface 308 facing proximally. The plug has a radially symmetric coupling handle 310 at its proximal end for attachment to a delivery and/or recapture catheter (not shown). When inserting plug 300 into the intra-bronchial device, distal movement of plug 300 into shaft 252 causes fingers 302 to cam radially inward until the distal end of plug 300 emerges from the distal end of shaft 252, at which point fingers 302 move outward to lock plug 300 in place. A proximal shoulder (not shown) may be provided on plug 300 to prevent the plug from advancing out the distal end of the intra-bronchial device. If removal of plug 300 is desired, a proximally directed force on plug 300 will cause fingers 302 to cam inward to allow the plug to be withdrawn through shaft 252.

Figure 30:
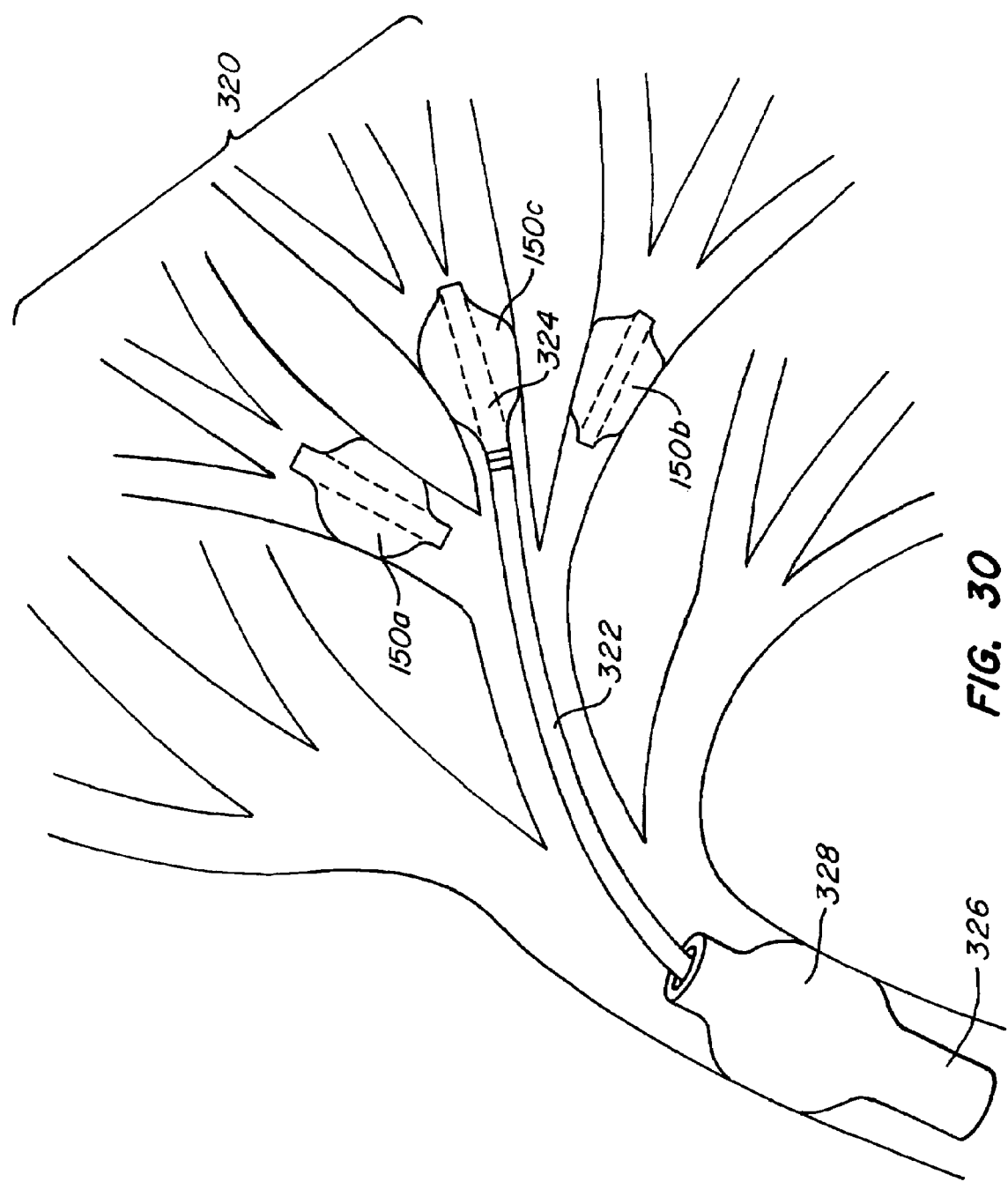
FIG. 30 shows the use of a plurality of intra-bronchial devices to treat a patient's lung.

FIG. 30 shows the use of the invention to compress a portion of a patient's lung. In this example, three intra-bronchial devices 150a, 150b and 150c are disposed in a portion 320 of the patient's lung. Devices 150a and 150b have been plugged and released from their delivery systems; device 150c is still connected to catheter 322 which communicates with the still-open lumen 324 of the device's central shaft. To compress lung portion 320, pressurized fluid is introduced into the patient's lung through sleeve 326 surrounding catheter 322. An expandable (e.g., inflatable, expanding metallic frame or braid) cuff 328 seals sleeve against the air passageway wall. Devices 150a-c prevent the pressurized fluid from entering lung portion 320. Inflation of one or more portions of the lung adjacent portion 320 will cause portion 320 to collapse, venting any air in lung portion 320 to the exterior of the patient through catheter 322. These devices cause effective lung tissue compression with the application of more than 10 mm Hg pressure above atmospheric pressure. By applying more pressure, the effect is made more rapid and complete: 25 mm Hg is better, 45 mm Hg is better still and more than 55 mm Hg is best.

The sleeve can be made of typical guide catheter materials with similar construction techniques and may be covered or comprised of silicone, polyurethane, biocompatible polymers, elastic balloon materials, semi-elastic balloon materials or a mesh composite. The balloon can be compliant or semi-compliant and can be made from polymers such as polyurethane or silicones. The cuff may be self expanding with the use of titanium alloys and these can be made from braid. Braided funnel shaped ends work very well to seal this device.

It is also possible to cause the target portion of the lung to collapse naturally, without hyperinflation of other portions of the lung. Once a lung region has been isolated, oxygen is absorbed from the air in a greater volume than $CO_2$ is deposited. This absorptive atelectasis or auto-atelectasis causes the isolated lung region to collapse, allowing remaining portions of the lung to expand into that space.

Figure 31:
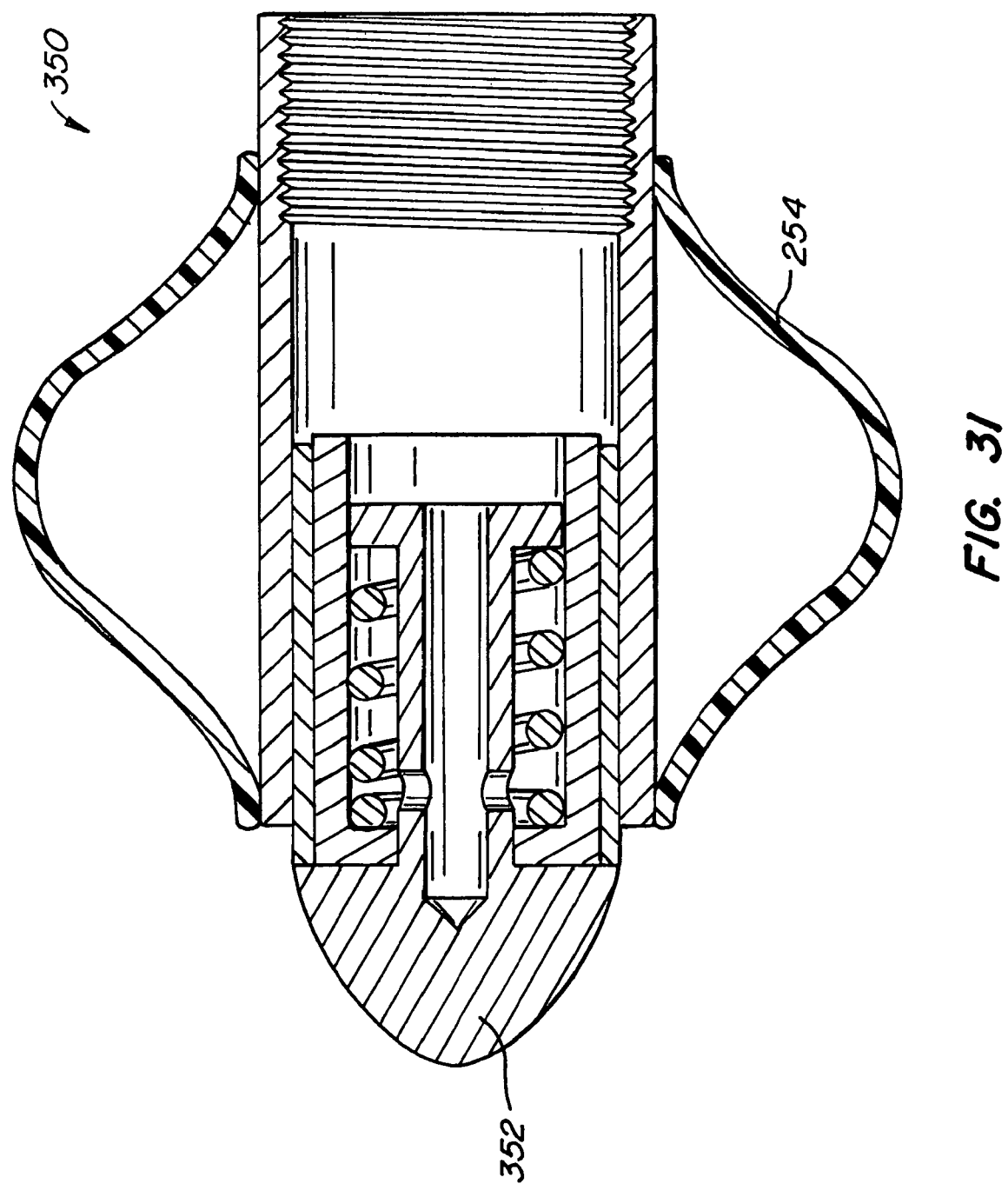
FIG. 31 is a cross-sectional view of a pressure relief system for use with the invention.
Figure 32:
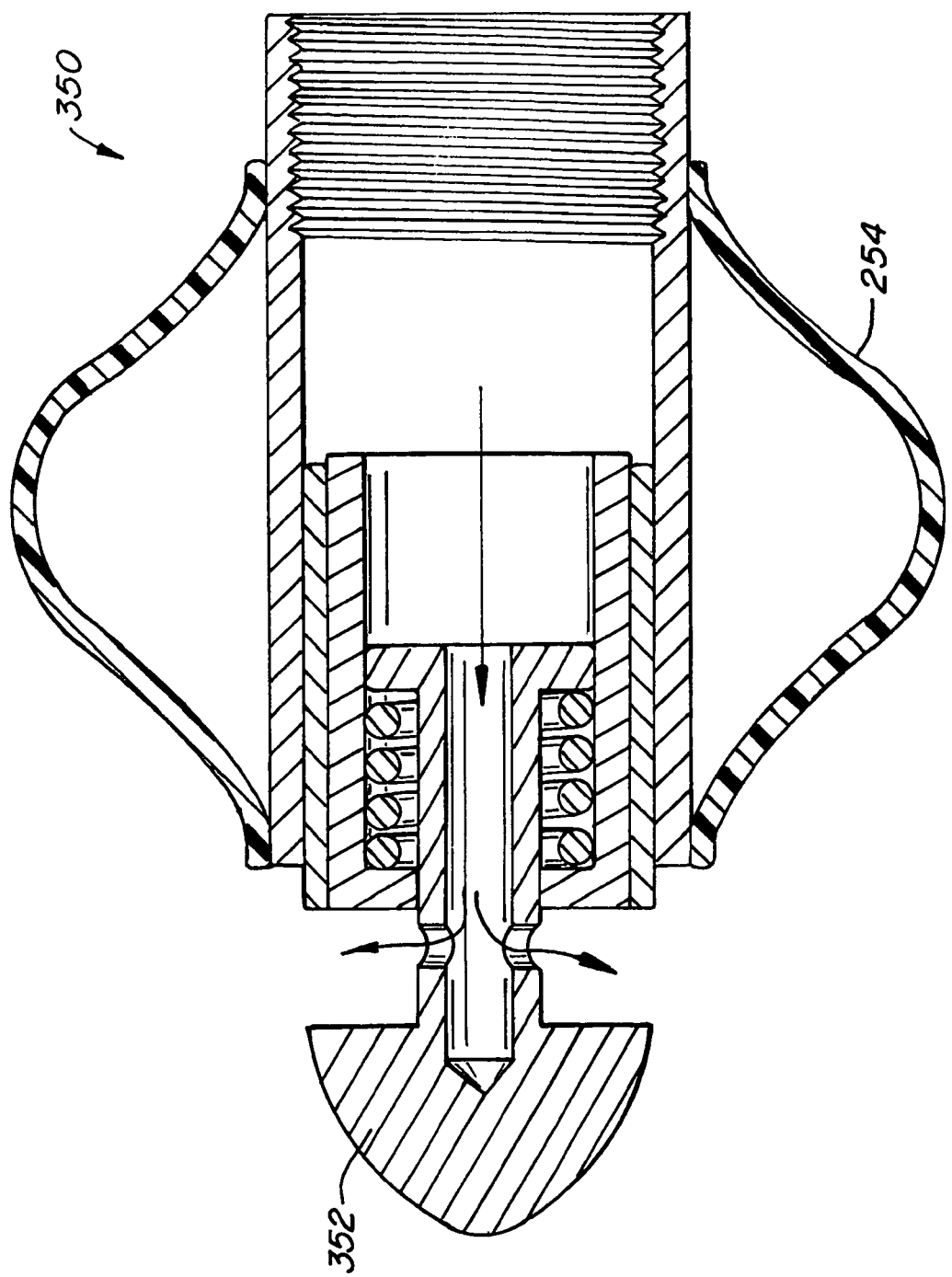
FIG. 32 shows the pressure relief system of FIG. 31 in an open position.

Over-expansion of the remaining portions of a lung after collapse of one portion of the lung can cause tissue tears and other injuries. FIGS. 31 and 32 illustrate a pressure relief system that minimizes the risk of such injuries. Intra-bronchial device 350 has a pressure relief valve 352 that opens (as shown in FIG. 32) when the differential pressure between the collapsing lung portion on the distal side of device 350 and the lung portions on the proximal side of device 350 exceeds a desired amount, such as, e.g., 2 mm Hg, 10 mm Hg, 20 mm Hg or 50 mm Hg. The greater the differential pressure, the greater the lung volume reduction, but also the greater the risk of complications. Alternatively, a maximum lung expansion may be targeted. For example, the pressure required to open the relief valve can be set such that the expanding lung tissue is not strained more than 150%. The pressure relief valve may also reside in an intra-bronchial device plug instead of being integral with the expandable intra-bronchial device itself.

FIG. 30 also shows aspects of a collateral flow detection system for use with this invention. Prior to attempting hyperinflation of the lung to collapse the target portion of the lung, this system can be used to check for the existence of collateral flow paths from the targeted lung portion 320 back to the remaining portions of the lung and the exterior of the patient. Air blended with a marker such as a detectable gas may be introduced into the lung through sleeve 326, and the air in the target region 320 may be monitored through catheter 322 by sniffing or sampling. If the marker gas is detected, collateral flow is occurring, either due to the presence of flow paths through degraded tissue, natural airways that still need to be plugged with intra-bronchial devices, or the failure of one or more implanted intra-bronchial devices. Gases that may be used for collateral flow detection are hyper-polarized gases such as helium, helium-3 and xenon-129. Other materials include Diethyl ether, Nitrous oxide, Chloroform, Cyclopropane, Trichloroethylene, Fluroxene, Halothane, Methoxyflurane, Enflurane, Isoflurane, Desflurane, Sevoflurane or components of these. Small amounts of CO can also be tolerated and used for this purpose.

Upon detection of collateral flow paths, one or more agents to block and clog the collateral flow paths may be introduced, e.g., through the intra-bronchial device delivery catheter so that it is installed in the isolated lung region. The agent will flow through any such collateral flow path. This treatment is intended to block flow of collateral pathways that are created by the degenerative disease. As such, treatments may need to be repeated periodically to block pathways that are newly formed by the disease progression. This can be easily done by coupling a delivery catheter to the intra-bronchial device and then by removing the central cap from the intra-bronchial device. This provides a direct conduit to the distal isolated lung region.

Microparticles can be used for blocking collateral flow in lung tissue. The microparticles preferably comprise a polymeric binder or other means to make controlled geometry particles. Suitable polymeric binder materials include poly (glycolic acid), poly-d,l-lactic acid, poly-l-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoester, poly(glycolic acid-caprolactone), polyanhydrides, polyphosphazines, albumin, casein, and waxes. Poly (d,l-lactic-co-glycolic acid) is commercially available from Alkermes, Inc. (Blue Ash, Ohio). A suitable product commercially available from Alkermes, Inc. is a 50:50 poly (d,l-lactic-co-glycolic acid) known as MEDISORB.RTM. 5050 DL. This product has a mole percent composition of 50% lactide and 50% glycolide. Other suitable commercially available products are MEDISORB.RTM. 6535 DL, 7525 DL, 8515 DL and poly(d,l-lactic acid) (100 DL). Poly(lactide-co-glycolides) are also commercially available from Boehringer Ingelheim (Germany) under its Resomer.RTM. mark, e.g., PLGA 50:50 (Resomer.RTM. RG 502), PLGA 75:25 (Resomer.RTM. RG 752) and d,l-PLA (Resomer.RTM. RG 206), and from Birmingham Polymers (Birmingham, Ala.). These copolymers are available in a wide range of molecular weights and ratios of lactic acid to glycolic acid.

Other materials include biocompatible polymers that are described in the US Pharmacopeia and include dextrans and other carbohydrate-based materials or derivatives thereof, polyethylene glycol, polyethylene oxide, polyvinyl alcohol, and starch. Additional materials include polyesters, such as polyglycolic acid, polylactic acid, poly-1,4-dioxa-2-one, polyoxaltes, polycarbonates, copolymers of polyglycolic acid and polylactic acid, polycaprolactone, poly-b-hydroxybutyrate, copolymers of epsilon-caprolactone and delta-valerolactone, copolymers of epsilon-caprolactone and DL-dilactide, and polyester hydrogels; polyvinylpyrrolidone; polyamides; gelatin; albumin; proteins; collagen; poly (orthoesters); poly(anhydrides); poly(alkyl-2-cyanoacrylates); poly(dihydropyrans); poly(acetals); poly(phosphazenes); poly(urethanes); poly(dioxinones); cellulose; agarose, agar, and starches, and derivatives of any of the aforementioned.

Block copolymers are another class of materials that are suitable for the present invention.

Protein microspheres are another class of materials that enables the present invention. For example, albumin can be cross-linked with a suitable cross-linker to generate particles for various applications including imaging. Other proteins suitable for enabling the present invention include recombinant or naturally occurring human, animal, or vegetable proteins, including collagen, gelatin, casein, soybean protein, vegetable protein, and keratin.

Liposomes, proliposomes, or microparticles containing fatty acids, lipids, or derivatives thereof will also enable the invention.

Synthetic polymeric particles comprised of HEMA (hydroxyethlymethacrylate), AEMA (aminoethyl methacrylate), DMEMA (N,N dimethyl amino) and other acrylates, acrylamides, methacrylamides, styrene, or any polymerizable material will also work in this application.

A viscous solution that reduces or blocks collateral flow in lungs may also be used. Viscous solutions for the present invention are preferably biocompatible solutions such as hydrogels or other substances including glycerol and aqueous solutions containing water soluble materials including cellulose derivatives, dextrans, starches, and any carbohydrate or carbohydrate based material or derivative thereof. Other aqueous solutions may contain synthetic polymers including povidone, PEG (polyethylene glycol or polyethylene oxide), polyvinyl alcohol, and diethyl aminoethyl (DEAE)—sephadex. Aqueous solutions may also contain proteins such as collagen and albumin. Other viscous solutions may contain non-aqueous cosolvents such as ethanol. Buffers, salts, and excipients may also be part of the formulation of thixotropic viscous solutions.

In one embodiment, a two-part sealant may be applied to areas of interest. One novel method involves applying one part of the sealant to a desired area in one lobe, and applying a second component to the other lobe. The two components may mix and solidify at a location between the lobes, or partially in both lobes such that flow is reduced. Sealant components for this application may include fibrin/thrombin, activated PEG/PEG-diamine, albumin/PEG, and albumin/glutaraldehyde sealants. The sealant is an implantable material that may contain hemostatic agents such as chitin derivatives including but not limited to carboxymethyl chitin and chitosan (1-100% deacetylated). The sealant components may also contain additives that affect viscosity, set time, adhesion, and biocompativility. The albumin component may be formulated in weight to weight ratios of 10-50% where the remaining mass balance is aqueous solutions of salts, buffers, and additives or combinations thereof. The other component of the sealant is a cross-linker containing glutaraldehyde or derivatives thereof in weight to volume ratios of 1-25% where the remaining balance is an aqueous solution with or without additives, salts, or buffers or combinations thereof. These solutions may be applied from dispensers that deliver a ratio of 1 unit volume of protein solution per 1 unit volume of cross-linker solution (1:1 protein:cross-linker) and may be applied in ratios up to 10 unit volumes of protein solution per unit volume of cross-linker solution. Furthermore, mixing may occur by passing the solutions through a static mixing tip with helical or other geometrical devices that enhance the mixing efficiency. Sealants prepared from these solutions contain 5-45% protein and 0.5-14% crosslinker.

Other suitable sealants and other agents are described in U.S. Pat. Appl. Publ. No. 2004/0052850; U.S. Pat. Appl. Publ. No. 2004/0081676; U.S. Ser. No. 11/008,577; U.S. Ser. No. 11/008,092; U.S. Ser. No. 11/008,094; U.S. Ser. No. 11/008,578; U.S. Ser. No. 11/008,649; U.S. Ser. No. 11/008,777; U.S. Ser. No. 11/008,087; U.S. Ser. No. 11/008,093; U.S. Ser. No. 11/008,580; and U.S. Ser. No. 11/008,782.

We have determined that many of these agents cause tissue binding to form localized adhesions or a bio-response that will help maintain a permanent volume reduction. With the introduction of these materials we are instigating one or more elements of a well understood tissue remodeling cascade process. The process includes tissue polymer decomposition and/or necrosis that leads to recruitment of cellular respondents that include one or more of the following: Neutrophils, white blood cells, macrophages, CD8+, MMP's, Interlukens, cytokins and protocylins. Then the tissue remodels to initiate tissue formation and thickening that culminates in the formation of tissue adhesions.

Other materials that can initiate this effect are cadmium, smoke artifacts, tars, materials that irritate tissue such as alcohols, solvents, organic solvents, acids, materials that are basic and materials that are acidic. These include compounds or materials that have pH levels between 1 and 6.9 with materials closest to 1 being a preferable acid material. Additionally, compounds or materials that have pH levels between 7.5 and 14 work very well but materials closest to 14 work best.

Materials that solidify such as glue compositions form a structure that is typically stiffer than the intrinsic stiffness of lung tissue. Specifically, pull tests of lung parenchema (comprised of alveoler sacks and collagen) sections show that the composite stiffness is very low. When we combine agents that form a stiffer structure than the underlying biomaterial or lung tissue, the modulus mismatch causes irritation, inflammation, tissue thickening, fibrosis, a remodeling cascade and adhesions that will promote and maintain lung volume reduction. Compositions that dry out or maintain viscosity levels above 2 centipoise (a measure of dynamic viscosity) generate shear and cause this stiffness mismatch to promote adhesions. Agents and hydrogel materials thicker than 10 centipoise work better. Our glutaraldehyde glue technology can produce compositions that have 15 centipoise viscosity and higher levels up to and beyond 150 centipoise. By increasing the glue cross linking properties, we can deliver agents that solidify to a gel or harder substance. Materials that gel to produce solids with a modulus greater than 10-20 centimeters of $H_2O$ will produce this same effect. Materials that are stiffer in a range between 20 and 100 centimeter of $H_2O$ are better. Materials that are stiffer than 100 cm $H_2O$ are preferable. We have developed several implantable materials with viscosity enhancing agents to promote these effects.

When applying an implantable hydrogel comprised of a biocompatible material, or an implantable liquid that undergoes a physical transition from a liquid to a gel or other solid such as solid adhesives, control of deposition is very important. Ways of controlling deposition include localized dispensing of the sealant through a suitable device containing a lumen, and also through the addition of agents that increase the viscosity of one or more components of the implantable material. Such agents include biocompatible materials with viscosities that are greater than those of water, and include glycerol, polymeric materials such as proteins, carbohydrate-based polymers and derivatives thereof, synthetic materials including polyethylene glycols (PEG), polyethylene oxides (PEO), polyvinyl pyrrolidone (PVP), polyvinyl alcohol and other components described in the "United States Pharmacopeia" and Rowe, R. C, et al., *Handbook of Pharmaceutical Excipients* $4^{th}$ edition 2003. Other materials for controlling viscosity include oils, lipids, and fatty acids, including oleic acid, and phosphocholines. Phase separation can be controlled with emulsifiers including poly sorbate. For sealants prepared by mixing two or more components, the viscosities of one or more of the components can be modified by adding an appropriate agent to control spreading after application. Viscosities of these components can range from 1 to 1000 centistokes (a measure of kinematic viscosity).

Deposition and control of spreading of sealants containing two or more components are also affected by the gel time, or set time, of the mixed sealant. Sealants with short set times are preferable to those with longer set times. Ideal set times for the present invention and method range from 1-600 seconds, and preferable from 1-60 seconds. Set time can be controlled by the addition of set time modifiers, including agents that reduce or increase the set time relative to the corresponding formulation lacking the set time modifier. An example of an agent that decreases the set time is carboxymethyl cellulose. An example of an agent that increases the set time is glycerol.

Glutaraldehyde, as currently processed and used in some commercial sealants, undergoes reversible reactions that cause reoccurring inflammation. These properties can be improved by chemical modification of the glutaraldehyde. One such modification includes glutaraldehyde condensation reactions, as described in "Bioconjugate Techniques" by G. T. Hermanson. This condensation involves the formation of derivatives of glutaraldehyde in aqueous solutions containing acid or base. This reaction can be monitored by ultraviolet spectroscopy at or near 280 and 234 nanometers. At 280 nanometers, pure glutaraldehyde has significant absorbance, and little or no absorbance at 234 nanometers when measured as an aqueous solution at 0.5% weight to volume. When glutaraldehyde is chemically modified, it has significant absorbance at 234 nanometers. These derivatives are effective cross-linking agents when used with nucleophilic substrates such as proteins, including albumins. Furthermore, sealants prepared from glutaralde hyde derivatives are adhesive in vivo, through chemical or mechanical means, or a combination of chemical and mechanical means.

Implantable materials for the present invention are any agents administered into tissue, including sealants, which may be comprised of hydrogels, proteins, or other biocompatible materials, that can be implanted into compromised tissue to benefit the patient. Examples of hydrogels include those prepared from natural sources including carbohydrate-based materials. Such materials include hyaluronans, hyaluronic acid, alginates, chitins, chitosans, and derivatives thereof. Proteins that enable the present invention include albumins, collagens, gelatins, and other proteins that can be cross-linked or that form solutions with viscosities greater than water. Other implantable materials include those prepared by mixing two or more components so that a viscous solution, gel, or solid is formed. Such implantable materials are prepared from a protein substrate where the protein is derived from natural, synthetic, or semi-synthetic processes. The protein may also be derived from recombinant DNA technology and may be isolated from cell-culture processes, as well as from transgenic plants and animals. Examples of proteins include albumins, collagens, and gelatins. Cross-linkers employed as part of the implantable material precursors include aldehydes, polyaldehydes, esters, and other chemical functionality suitable for cross-linking protein(s). Examples of homobifunctional cross-linking agents are described in "Bioconjugate Techniques" by G. T. Rermanson.

The implant components, including the cross-linking agent and the substrate, can be formulated at a pH in the range of 5-10 by adjusting the pH and/or by adding suitable buffers in the range of 1-500 mM. Examples of buffers include phosphate, carbonate, bicarbonate, borate, or imidazole, or mixtures thereof. Additionally, additives or stabilizers may be added to improve the stability of one or more of the components. Furthermore, imaging agents may be added to allow for detection of the material. Such agents include iodine, iodine compounds, metals such as gadolinium, radioisotopes, and other compounds for gamma scintigraphy, magnetic resonance imaging, fluoroscopy, CT, SPECT and other imaging modalities. Additionally, the material may be formulated such that the mechanical properties are suitable for applications in the specific tissue to which the imp lantable material is applied. Such properties include elasticity, modulus, stiffness, brittleness, strain, cohesion, adhesion, and stress. Agents for modifying the properties include fillers, plasticizers, and adhesion modifiers. Furthermore, the implant may induce a natural adhesive mechanism with or without the addition of chemical agents which may be added to the implant to induce a natural response. Such agents include particles in the range of 100 nm to 1 millimeter. Agents include chemical or biochemical agents (proteins or nucleic acids) that induce a natural response. Examples of such agents include bleomycin, cytokines and chemokines, and single stranded RNA molecules.

Intra-bronchial devices according to this invention may be delivered through the working channel of a bronchoscope. Alternatively, the lung access system described in the U.S. patent application filed of even date herewith titled "Lung Access Device and Method," may be used to deliver the devices to a patient's lung. This latter delivery method may be used when the diameter of a bronchoscope is too small for the device to be delivered. One advantage of using an intra-bronchial device with a larger, collapsed delivery diameter is that the expansion ratio from delivery diameter to deployed diameter may be made smaller than, e.g., 7.5, more preferably smaller than 6, more preferably smaller than 5, more preferably smaller than 4, and most preferably smaller than 3.

Another advantage of using the alternative outside the scope delivery system is that the delivered devices are not limited in length since they can be delivered outside the constraints of the scope channel. The scope path to the upper airways, where the most tissue damage normally resides, requires very small radius bends to be formed in the bronchoscope to gain access. Long implant devices that would straighten the scope if delivered through the channel can now be delivered outside the channel while the target region continues to be imaged through the scope optics.

In addition, it is desirable to make the implant longer than its diameter to provide stability from, e.g., rotating in the airway. These relative dimensions also make it much easier to capture the end of the device later to access the through-lumen or to recover or move the device. Implant devices that exceed 4 mm in length can now be delivered easily using this system. Devices longer than 5 mm will work better, devices longer than 10 mm are better, devices longer than 20 mm are preferable, devices longer than 25 mm, 30 mm, and 35 mm will anchor much better.

These devices can be made from all biocompatible plastics, metals, ceramics, shape memory alloys and carbon based fiber or polymers. The catheter devices can be lined with fluoro polymers and reinforced with metal or polymer fiber or wire braid or by using coils of similar materials. The wire elements that guide devices can be made from steel or titanium alloys or other metals that do not present artifacts in MRI equipment. Other materials including shape memory alloys such as nickel- and titanium-based metals that are comprised of more than 40% titanium would perform well in that they can be made in an anisotropic way to provide different properties with bending and torque.

In some embodiments, one or more of the delivery and deployment catheters may have multiple lumens. For example, a multi-lumen catheter could be used to both inflate the intra-bronchial device and deliver glue or another substance (such as those described above) outside of, and either distal or proximal to, the intra-bronchial device. Sheaths, needles and other devices may be used to deploy such substances.

Another use of an extra-catheter lumen is as a return path. As long as the pressure drop over the return path is less than the pressure required to inflate the intra-bronchial device, air or the inflation fluid will preferentially flow down the return path. The pressure can be controlled with the delivery rate of the inflation fluid. This return path can also act as a pressure relief conduit to control the maximum inflation pressure applied to the balloon.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of selectively compressing a lung of a patient comprising:
    selecting one of a right lung or a left lung;
    advancing a device through a trachea of the patient into the selected lung;
    venting a first portion of the selected lung to the exterior of the patient through the device the first portion being targeted for compression;
    isolating the first portion of the selected lung from a second portion of the selected lung adjacent the first portion; and
    delivering sufficient pressurized fluid through one or more ports of the device to air passageways of the second portion of the selected lung to compress the first portion of the selected lung.

2. The method of claim 1 wherein the isolating step comprises delivering an expandable device to an air passageway communicating with and proximal to the first portion of the selected lung.

3. The method of claim 2 wherein the step of venting comprises venting the expandable device.

4. The method of claim 1 wherein the isolating step comprises delivering a plurality of expandable devices to air passageways communicating with and proximal to the first portion of the selected lung.

5. The method of claim 1 wherein the step of delivering pressurized fluid comprises delivering pressurized fluid at a pressure of at least 10 mm Hg above atmospheric pressure.

6. The method of claim 5 wherein the step of delivering pressurized fluid comprises delivering pressurized fluid at a pressure of at least 25 mm Hg above a atmospheric pressure.

7. The method of claim 6 wherein the step of delivering pressurized fluid comprises delivering pressurized fluid at a pressure of at least 45 mm Hg above atmospheric pressure.

8. The method of claim 7 wherein the step of delivering pressurized fluid comprises delivering pressurized fluid at a pressure of at least 55 mm Hg above atmospheric pressure.

9. The method of claim 1 further comprising permitting fluid to enter the first portion of the selected lung when a difference between a fluid pressure within the first portion of the selected lung and a fluid pressure in the second portion of the selected lung exceeds about 2 mm Hg.

10. The method of claim 9 wherein the permitting step comprises permitting fluid to enter the first portion of the selected lung when a difference between the fluid pressure within the first portion of the selected lung and the fluid pressure in the second portion of the selected lung exceeds about 10 mm Hg.

11. The method of claim 9 wherein the permitting step comprises permitting fluid to enter the first portion of the selected lung when a difference between the fluid pressure within the first portion of the selected lung and the fluid pressure in the second portion of the selected lung exceeds about 20 mm Hg.

12. The method of claim 9 wherein the permitting step comprises permitting fluid to enter the first portion of the selected lung when a difference between the fluid pressure within the first portion of the selected lung and the fluid pressure in the second portion of the selected lung exceeds about 50 mm Hg.

13. A method of compressing a first portion of one of a right lung or a left lung of a patient comprising:
    selecting one of the right lung or the left lung;
    isolating air passageways of a first portion of the selected lung from a second portion of the selected lung adjacent the first portion;
    isolating the second portion of the selected lung from the atmosphere;
    providing a vent connecting the first portion of the selected lung to the atmosphere; and
    delivering sufficient pressurized fluid to the air passageways of the second portion of the selected lung to compress the first portion of the selected lung.

14. The method of claim 13 wherein the step of isolating the first portion of the selected lung comprises delivering an expandable device to an air passageway communicating with and proximal to the first portion of the selected lung.

15. The method of claim 14 wherein the step of providing a vent comprises venting the expandable device.

16. The method of claim 14 further comprising permitting fluid to enter the first lung portion when a difference between fluid pressure within the first lung portion and fluid pressure in the second lung portion exceeds about 2 mm Hg.

17. The method of claim 13 wherein the step of delivering pressurized fluid comprises delivering pressurized fluid at a pressure of at least 10 mm Hg above atmospheric pressure.

* * * * *